United States Patent [19]

Atsumi et al.

[11] Patent Number: 4,839,350
[45] Date of Patent: Jun. 13, 1989

[54] CEPHALOSPORIN COMPOUNDS AND THE PRODUCTION THEREOF

[75] Inventors: Kunio Atsumi; Kenji Sakagami, both of Kawasaki; Yuichi Yamamoto, Yokohama; Takashi Yoshida, Tokyo; Ken Nishihata; Shinichi Kondo, both of Yokohama; Shunzo Fukatsu, Tokyo, all of Japan

[73] Assignees: Meiji Seika Kaisha, Ltd.; Susumu Mitsuhashi, both of Tokyo, Japan

[21] Appl. No.: 36,124

[22] Filed: Apr. 7, 1987

Related U.S. Application Data

[63] Continuation of Ser. No. 769,746, Aug. 27, 1985, abandoned.

[30] Foreign Application Priority Data

Sep. 7, 1984 [JP] Japan .................... 59-186464
Jul. 18, 1985 [JP] Japan .................... 60-157005

[51] Int. Cl.[4] .................... A61K 31/545; C07D 501/24
[52] U.S. Cl. .................... 514/202; 514/206; 540/222; 540/227
[58] Field of Search ............. 540/222, 227; 514/202, 514/206

[56] References Cited

U.S. PATENT DOCUMENTS

| 4,255,423 | 3/1981 | Beattie | 540/222 |
| 4,307,116 | 12/1981 | Farge | 540/227 |
| 4,482,551 | 11/1984 | Furlenmeier | 540/227 |

FOREIGN PATENT DOCUMENTS

0053074 6/1982 European Pat. Off. .

OTHER PUBLICATIONS

Dunn, J. Antimicrobial Chemotherapy (1982), 10, Supplement C, pp. 1–10.

Primary Examiner—Robert J. Warden
Assistant Examiner—Robert Benson
Attorney, Agent, or Firm—Larson and Taylor

[57] ABSTRACT

A class of new caphalosporin compounds (syn-isomer) is now provided, which is useful as antibacterial agent and is represented by the general formula (I)

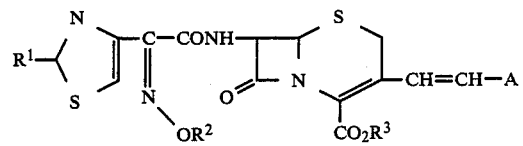

wherein $R^1$ is an amino group or a protected amino group; $R^2$ is a lower alkyl group, a carboxymethyl group or a protected carboxymethyl group; $R^3$ is a hydrogen atom, a salt-forming cation or a carboxyl-protecting group; A is an unsubstituted or substituted phenyl group, an unsubstituted or substituted furyl group, an unsubstituted or substituted thiazolyl group or an unsubstituted or substituted 3-lower-alkylthiazolio group, and a pharmaceutically acceptable salt or ester thereof.

14 Claims, No Drawings

CEPHALOSPORIN COMPOUNDS AND THE PRODUCTION THEREOF

This application is a continuation of application Ser. No. 769,746, filed Aug. 27, 1985, now abandoned.

SUMMARY OF THE INVENTION

This invention relates to a new cephalosporin compound and a pharmaceutically acceptable salt or ester thereof which are useful as antibacterial agent. More particularly, this invention relates to a new cephalosporin compound (as syn-isomer) which bears an α-(substituted imino)-α-(2-aminothiazolyl)-acetyl group as a side chain at the 7-position and a β-substituted vinyl group as a side chain at the 3-position of the cephem nucleus. This invention also relates to a pharmaceutical composition comprising the new cepahlosporin compound as active ingredient. This invention further relates to a process for the production of the new cephalosporin compound.

BACKGROUND OF THE INVENTION

Some β-lactam compounds which are closely related to the new cephalosporin compounds of this invention are known as disclosed in Japanese Patent Application first publication "Kokai" No. 124790/80, No. 122383/81 and No. 76088/84, and U.K. patent application first publication No. 2128990 A. These known cephalosporin compounds which are disclosed in said Japanese patent application first publications have a β-substituted vinyl group as the side chain at the 3-position of the cephem nucleus, similarly to the cephalosporin compounds according to this invention. However, the new cephalosporin compounds of this invention are different from the above-mentioned known cephalosporin compounds in respect of the kind of the substituent born on the β-position of the β-substituted vinyl group at the 3-position of the cephem nucleus.

Cephalosprin-type antibiotics are known to be highly and broadly active against a variety of gram-positive and gram-negative bacteria. Various kinds of semi-synthesized cephalosporin compounds have already been available commercially and applied clinically for the therapeutic treatment of various infections diseases. But, only a very few ones amongst these semi-synthesized cephalosporin compounds are practically effective against the strains of bacteria of the genus Pseudomonas and Proteus. These known cephalosporin compounds are also degradable by a β-lactamase which is produced by some resistant strains of bacteria, and they exhibit only a poor activity against some resistant strains of bacteria which have now been a target of clinical treatments of bacterial infections (see: W. E. Wick "Cephalosporins and Penicillins, Chemistry and Biology", edited by E. H. Flynn, Academic Press, New York, N.Y., 1972, Chapter 11.)

We, the present inventors, have now succeeded in preparing new cephalosporin compounds represented by the general formula (I) shown below, and have found that said new cephalosporin compounds exhibit activity in a very wide range of the antibacterial spectrum and that these new compounds are highly active not only against a variety of gram-positive and gram-negative bacteria but also against some resistant strains of bacteria.

DETAILED DESCRIPTION OF THE INVENTION

According to a first aspect of this invention, there is provided a new cephalosporin compound of the general formula (I)

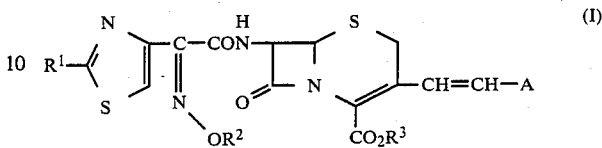

wherein $R^1$ is an amino group or a protected amino group; $R^2$ is a lower alkyl group, a carboxymethyl group or a protected carboxymethyl group; $R^3$ is a hydrogen atom, a salt-forming cation or a carboxyl-protecting group; A is an unsubstituted or substituted phenyl group, an unsubstituted or substituted furyl group, an unsubstituted or substituted thiazolyl group or an unsubstituted or substituted 3-lower-alkylthiazolio group, and a pharmaceutically acceptable salt or ester of said cephalosporin compound.

The cephalosporin compound of the formula (I) according to this invention includes two isomers, namely (E)-isomer (i.e., a trans-isomer) and (Z)-isomer (i.e., a cis-isomer), depending on the relative positions of the substituents and the hydrogen atoms attached to the vinylic double bond of the β-substituted vinyl group at the 3-position of the cephem nucleus. The cephalosporin compound of this invention, therefore, covers the (E)-isomer, the (Z)-isomer and the mixture thereof. The (Z)-isomer of the cephalosporin compound according to this invention is of such a form in which the group A and the cephem moiety take "cis"-position around the vinylic double bond of the vinyl group at the 3-position as shown in the general formula (I). The (E)-isomer of the cephalosporin compound is of such form in which the group A and the cephem moiety take "trans"-position aroung the vinylic double bond of the vinyl group at the 3-position of the cephem nucleus.

Some of the terms used in this specification have the meanings as defined below:

The term "lower" means that an alkyl or alkoxyl or alkanoyl group concerned is containing 1 to 6 carbon atoms, unless otherwise stated. The amino-protecting group, such as the amino-protecting group present in the protected amino group which $R^1$ may represent, includes a conventional amino-protecting group which may easily be removed by acid hydrolysis, for example, an alkoxycarbonyl group such as tert.-butoxycarbonyl group; and acyl group such as a formyl group and a chloroacetyl group; and a trityl group.

The "protected carboxymethyl group" which $R^2$ represents is such a carboxymethyl group of which the carboxyl group has been protected by esterification with a lower alkyl group, e.g., methyl, ethyl, propyl, n-butyl and t-butyl or an aryl group such as phenyl or an aralkyl group such as benzyl.

The salt-forming cation which $R^3$ represents is a conventional metal cation and may include cation of an alkali metal, an alkaline earth metal and ammonium. Sodium cation is preferred. The carboxyl-protecting group which $R^3$ represents is a carboxyl-protecting group conventionally used for cephalosporins and may include an aryl group, a lower alkyl group, a lower-alkoxymethyl group, a lower-alkylthio methyl group and a lower-alkanoyloxymethyl group and the like. The group $R^3$ may also include a metabolically unstable group which is easily hydrolyzed and cleaved in vivo and which may include, for example, a lower-alkoxycarbonyloxyalkyl group, a lower-alkylcarbonyloxyalkyl group, an unsubstituted or substituted (2-oxo-1,3-dioxolene-4-yl) methyl group and the like.

"Unsubstituted or substituted phenyl group" which A represents includes a phenyl group; a phenyl group having a lower alkyl substituent, for example, p-tolyl; a halogenated phenyl group such as o-fluorophenyl, and a lower alkoxyphenyl group such as p-anisyl.

"Unsubstituted or substituted furyl group" which A represents includes a 2-furyl group, a 3-furyl group and a 5-nitro-2-furyl group.

"Unsubstituted or substituted thiazolyl group" which A represents includes thiazol-2-yl group, thiazol-4-yl group, thiazol-5-yl group, a 2-lower-alkylthiazol-5-yl group (e.g., 2-methylthiazol-5-yl), 4-methylthiazol-5-yl group, a 4-halo-thiazol-5-yl group and a 2,4-di-halo-thiazol-5-yl group.

"Unsubstituted or substituted 3-lower-alkylthiazolio group" which A represents includes a 3,4-dimethyl-5-thiazolio group.

According to a preferred, first embodiment of the first aspect invention, there is provided a cephalosporin compound of the general formula (Ia)

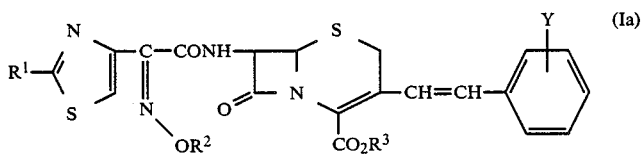

wherein $R^1$ is an amino group or a protected amino group, $R^2$ is a lower alkyl group, a carboxymethyl group or a protected carboxymethyl group, $R^3$ is a hydrogen atom, a salt-forming cation or a carboxyl-protecting group, and Y is a hydrogen atom, a lower alkyl group, a lower alkoxyl group or a halogen atom.

According to a preferred, second embodiment of the first aspect invention, there is provided a cephalosporin compound of the general formula (Ib)

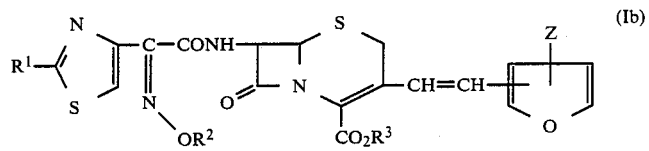

wherein $R^1$ is an amino group or a protected amino group, $R^2$ is a lower alkyl group, a carboxymethyl group or a protected carboxymethyl group, $R^3$ is a hydrogen atom, a salt-forming cation or a carboxyl-protecting group, Z is a hydrogen atom, nitro group or a halogen atom.

According to a preferred, third embodiment of the first aspect invention, there is provided a cephalosporin compound of the general formula (Ic)

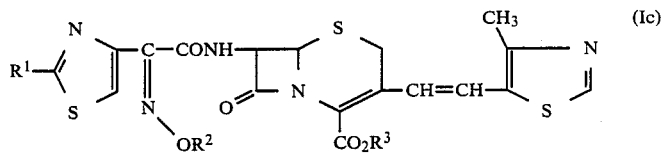

wherein $R^1$ is an amino group or a protected amino group, $R^2$ is a lower alkyl group, a carboxymethyl group or a protected carboxymethyl group, and $R^3$ is a hydrogen atom, a salt-forming cation or a carboxyl-protecting group.

According to a preferred, fourth embodiment of the first aspect invention, there is provided a cephalosporin compound of the general formula (Id)

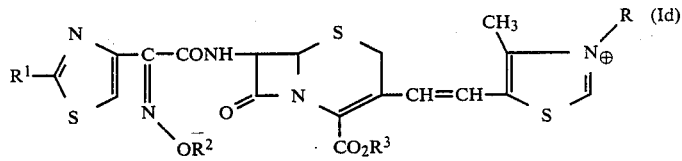

wherein $R^1$ is an amino group or a protected amino group, $R^2$ is a lwoer ($C_1$–$C_6$) alkyl group, a carboxymethyl group or a protected carboxymethyl group, $R^3$ is a hydrogen atom, a salt-forming cation or a carboxyl-protecting group, and R is a lower alkyl group.

According to a preferred, fifth embodiment of the first aspect invention, there is provided a cephalosporin compound of the general formula (Ie)

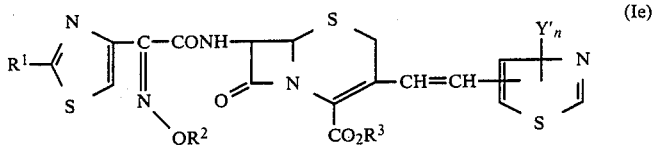

wherein $R^1$ is an amino group or a protected amino group, $R^2$ is a lower ($C_1$–$C_6$) alkyl group, a carboxymethyl group or a protected carboxymethyl group, $R^3$ is a hydrogen atom, a salt-forming cation or a carboxyl-protecting group, and $Y'$ is a hydrogen atom or a halogen atom, and n is a whole number of 1 or 2.

According to a preferred, sixth embodiment of the first aspect invention, there is provided a cephalosporin compound of the general formula (If)

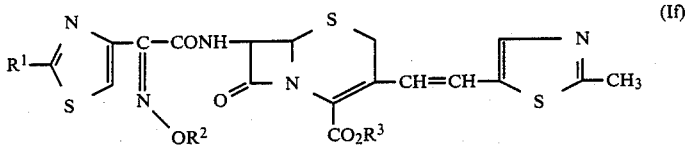

wherein $R^1$ is an amino group or a protected amino group, $R^2$ is a lower ($C_1$–$C_6$) alkyl group, a carboxymethyl group or a protected carboxymethyl group, and $R^3$ is a hydrogen atom, a salt-forming cation or a carboxyl-protecting group.

Preferred examples of the new cephalosporin compound of the formula (I) or of the formula (Ia) to (If) according to this invention are listed below:

(A) 7-[2-methoxyimino-2-(2-tritylaminothiazol-4-yl)acetamido]-3-(2-phenylvinyl)-3-cephem-4-carboxylic acid (syn-isomer, trans-isomer, or syn-isomer, cis-isomer).

(B) 7-[2-methoxyimino-2-(2-aminothiazol-4-yl)acetamido]-3-(2-phenylvinyl)-3-cephem-4-carboxylic acid (syn-isomer, trans-isomer, or syn-isomer, cis-isomer).

(C) 7-[2-methoxyimino-2-(2-aminothiazol-4-yl)acetamido]-3-[2-(o-fluorophenyl)vinyl]-3-cephem-4-carboxylic acid (syn-isomer, trans-isomer, or syn-isomer, cis-isomer).

(D) 7-[2-methoxyimino-2-(2-tritylaminothiazol-4-yl)acetamido]-3-[2-(2-o-fluorophenyl)vinyl]-3-cephem-4-carboxylic acid (syn-isomer, trans-isomer, or syn-isomer, cis-isomer).

(E) 7-[2-methoxyimino-2-(2-tritylaminothiazol-4-yl)acetamido]-3-[2-(2-furyl)vinyl]-3-cephem-4-carboxylic acid (syn-isomer, trans-isomer, or syn-isomer, cis-isomer).

(F) 7-[2-methoxyimino-2-(2-aminothiazol-4-yl)acetamido]-3-[2-(2-furyl)vinyl]-3-cephem-4-carboxylic acid (syn-isomer, trans-isomer, or syn-isomer, cis-isomer).

(G) 7-[2-methoxyimino-2-(2-tritylaminothiazol-4-yl)acetamido]-3-[2-(5-nitro-2-furyl)vinyl]-3-cephem-4-carboxylic acid (syn-isomer, trans-isomer, or syn-isomer, cis-isomer).

(H) 7-[2-methoxyimino-2-(2-aminothiazol-4-yl)acetamido]-3-[2-(5-nitro-2-furyl)vinyl]-3-cephem-4-carboxylic acid (syn-isomer, trans-isomer, or syn-isomer, cis-isomer).

(I) 7-[2-methoxyimino-2-(2-aminothiazol-4-yl)acetamido]-3-[2-(thiazol-2-yl)vinyl]-3-cephem-4-carboxylic acid (syn-isomer, trans-isomer, or syn-isomer, cis-isomer).

(J) 7-[2-methoxyimino-2-(2-aminothiazol-4-yl)acetamido]-3-[2-(thiazol-4-yl)vinyl]-3-cephem-4-carboxylic acid (syn-isomer, trans-isomer, or syn-isomer, cis-isomer).

(K) 7-[2-methoxyimino-2-(2-tritylaminothiazol-4-yl)acetamido]-3-[2-(thiazol-5-yl)vinyl]-3-cephem-4-carboxylic acid (syn-isomer, trans-isomer, or syn-isomer, cis-isomer).

(L) 7-[2-methoxyimino-2-(2-aminothiazol-4-yl)acetamido]-3-[2-(thiazol-5-yl)vinyl]-3-cephem-4-carboxylic acid (syn-isomer, trans-isomer, or cyn-isomer, cis-isomer).

(M) 7-[2-methoxyimino-2-(2-tritylaminothiazol-4-yl)acetamido]-3-[2-(4-methylthiazol-5-yl)vinyl]-3-cephem-4-carboxylic acid (syn-isomer, trans-isomer, or cyn-isomer, cis-isomer).

(N) 7-[2-t-butoxycarbonylmethoxyimino-2-(2-tritylaminothiazol-4-yl)acetamido]-3-[2-(4-methylthiazol-5-yl)vinyl]-3-cephem-4-carboxylic acid (syn-isomer, trans-isomer, or syn-isomer, cis-isomer).

(O) 7-[2-carboxymethoxyimino-2-(2-aminothiazol-4-yl)acetamido]-3-[2-(4-methylthiazol-5-yl)vinyl]-3-cephem-4-carboxylic acid (syn-isomer, trans-isomer, or syn-isomer, cis-isomer).

(P) 7-[2-methoxyimino-2-(2-aminothiazol-4-yl)acetamido]-3-[2-(4-methylthiazol-5-yl)vinyl]-3-cephem-4-carboxylic acid (cyn-isomer, trans-isomer, or cyn-isomer, cis-isomer).

(Q) 7-[2-methoxyimino-2-(2-aminothiazol-4-yl)acetamido]-3-[2-(2-methylthiazol-5-yl)vinyl]-3-cephem-4-carboxylic acid (syn-isomer, trans-isomer, or syn-isomer, cis-isomer).

(R) 7-[2-methoxyimino-2-(2-tritylaminothiazol-4-yl)acetamido]-3-[2-(2-methylthiazol-5-yl)vinyl]-3-cephem-4-carboxylic acid (syn-isomer, trans-isomer, or syn-isomer, cis-isomer).

(S) 7-[2-methoxyimino-2-(2-aminothiazol-4-yl)acetamido]-3-[2-(4-chlorothiazol-5-yl)vinyl]-3-cephem-4-carboxylic acid (syn-isomer, trans-isomer, or cyn-isomer, cis-isomer).

(T) 7-[2-methoxyimino-2-(2-amino-thiazol-4-yl)acetamido]-3-[2-(2,4-dichlorothiazol-5-yl)vinyl]-3-cephem-4-carboxylic acid (syn-isomer, trans-isomer, or syn-isomer, cis-isomer).

(U) 7-[2-methoxyimino-2-(2-tritylaminothiazol-4-yl)acetamido]-3-[2-(3,4-dimethyl-5-thiazolio)vinyl]-3-cephem-4-carboxylic acid (syn-isomer, trans-isomer, or syn-isomer, cis-isomer) iodide or trifluoroacetate.

(V) 7-[2-methoxyimino-2-(2-aminothiazol-4-yl)acetamido]-3-[2-(3,4-dimethyl-5-thiazolio)vinyl]-3- cephem-4-carboxylic acid (syn-isomer, trans-isomer, or syn-isomer, cis-isomer) iodide or trifluoroacetate.

Each of the particular cephalosporin compounds as listed above may also be in the form of its carboxylate (at the carboxyl group at the 2-position of the cephem nucleus), for example, its sodium salt, its methyl ester, its ethyl ester, its diphenylmethyl ester, its p-methoxybenzyl ester, its pivaloyloxymethyl ester and its (5-methyl-2-oxo-1,3-dioxolene-4-yl)methyl ester.

The new compound of the formula (I) according to this invention may be prepared by any one of the following two methods.

Method 1:

In this method 1, a 7-aminocephalosporanic acid compound of the formula (II)

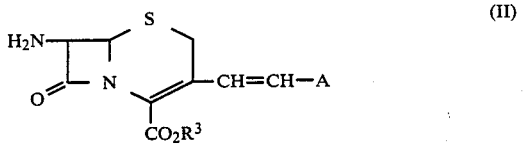

wherein $R^3$ and A are as defined above, or a reactive derivative (such a derivative made reactive at the 7-amino group as shown in the formula) of the compound of the formula (II) or a salt thereof is reacted with a 2-(2-aminothiazol-4-yl)-2-alkoxyiminoacetic acid compound of the formula (III)

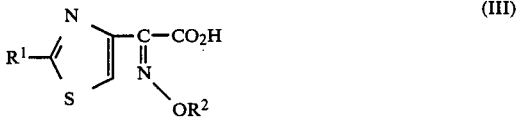

wherein $R^1$ and $R^2$ are as defined above, or a reactive acid derivative (such a derivative made reactive at the carboxyl group as shown in the formula) of the compound of the formula (III) or a salt thereof.

Examples of the reactive derivative at the amino group of the compound (II) include such an imino derivative of Shiff-base type which may be obtained by reaction of the compound (II) with a carbonyl compound such as an aldehyde or ketone, or an enamine-type isomer (tautomer) of said imino derivative; such a silyl derivative which may be obtained by reaction of the compound (II) with a silyl compound such as bis-(trimethylsilyl)acetamide; or such a derivative which may be obtained by reaction of the compound (II) with phosphorus trichloride or phosgene.

Appropriate examples of the salts of the compound (II) or (III) include an acid-addition salt thereof, for example, a salt of the compound (II) or (III) with an organic acid such as acetic acid, maleic acid, tartaric acid, benzenesulfonic acid, toluenesulfonic acid; a salt of the compound (II) or (III) with an inorganic acid such as hydrochloric acid, hydrobromic acid, sulfuric acid, phosphoric acid; a metal salt (carboxylate) of the compound (II) or (III) with an alkali metal such as sodium and potassium or with an alkaline earth metal such as calcium and magnesium; ammonium salt (carboxylate) of the compound (II) or (III); an amine salt of the compound (II) or (III) with an organic amine such as triethylamine and dicyclohexylamine.

Suitable examples of the reactive derivative at the carboxyl group of the compound (III) include an acid halide, an acid azide, an acid anhydride, an activated amide and an activated ester of the compound (III), and especially they may be an acid chloride or an acid bromide of the compound (III); a mixed acid anhydride of the compound (III) with an acid, for example, with a substituted phosphoric acid such as dialkylphosphoric acid, phenylphosporic acid, diphenylphosphoric acid, dibenzyl-phosphoric acid, a halogenated phosphoric acid, with a dialkyl phosphosphoric acid, with sulfurous acid, with thio-sulfuric acid, with sulfuric acid, with an alkyl carbonate such as methyl carbonate and ethyl carbonate, with an aliphatic carboxylic acid such as pivalic acid, valeric acid, isovaleric acid, 2-ethylacetic acid and trichloroacetic acid, or with an aromatic carboxylic acid such as benzoic acid; a symmetrical acid anhydride of the compound (III); an activated amide of the compound (III) formed with imidazole, 4-substituted imidazole, dimethylpyrazole, triazole or tetrazole; an activated ester of the compound (III) such as cyanomethyl ester, methoxymethyl ester, dimethyliminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester or 8-quinolylthio ester; or an ester of the compound (III) formed with a N-hydroxyl compound such as N,N-dimethylhydroxylamine, 1-hydroxy-2-(1H)-pyridone, N-hydroxysuccinimide, N-hydroxyphthalimide or 1-hydroxy-6-chloro-1H-benzotriazole.

These reactive derivatives of the compound (II) may be properly selected depending on the nature of the compound (III) to be reacted therewith.

The reaction of condensing the compound (II) with the compound (III) may usually be conducted in a conventional unreactive solvent such as water, acetone, dioxane, acetonitrile, chloroform, methylene chloride, ethylene chloride, tetrahydrofurane, ethyl acetate, N,N-dimethylformamide, pyridine, or in any other solvent which exerts no adverse effect on the progress of this reaction. These solvents may be used as a mixture with water.

In the case where the compound (III) is used in the form of a free acid or in the form of a salt, the reaction may preferably be conducted in the presence of a condensing agent. Examples of such a condensing agent may be N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; phosphorous acid trialkylester; ethyl polyphosphate; isopropyl polyphosphate; phosphorus oxychloride; phosphorus trichloride; thionyl chloride; oxalyl chloride; triphenylphosphine; 2-ethyl-7-hydroxybenzoisoxazolium salt; 2-ethyl-5-(m-sulfophenyl)isoxazolium hydroxide (intramolecular salt); 1-(p-chlorobenzenesulfonyloxy)-6-chloro-1H-benzotriazole; Vilsmeier reagent as prepared from reaction of dimethylformamide with thionyl chloride, phosgene and phosphorus oxychloride.

This reaction according to Method 1 may also be conducted in the presence of an inorganic or organic base. Examples of these inorganic and organic bases may be an alkali metal hydrogen carbonate such as sodium hydrogen carbonate or potassium hydrogen carbonate, an alkali metal carbonate such as sodium carbonate or potassium carbonate, an alkaline earth metal carbonate such as calcium carbonate, a tri-(lower-)alkyl amine such as trimethylamine or triethylamine, pyridine, N-(lower)alkylmorpholine, N,N-di-(lower)alkylbenzylamine.

The reaction as above may be carried out at a noncritical temperature, and may usually be conducted under cooling or under heating.

The product compound of the formula (I) which has been prepared by the above reactions for the preparation thereof, if desired, may then be subjected to further conventional step(s) for removal of the remaining carboxyl-protecting group and/or the remaining amino-protecting group therefrom, and/or to further conventional step(s) for converting the carboxyl group(s) of the product compound (I) into a metabolically unstable, non-toxic ester (carboxylate) group. The method for removal of the carboxyl-protecting group and/or the amino-protecting group may properly be chosen according to the nature of the protecting groups to be removed.

The amino-protecting group may be removed from the product compound (I) by a conventional deprotecting technique, for example, by hydrolysis or reduction, and for such a product compound bearing an acyl group as the amino-protecting group to be removed, it is feasible to subject such product compound (I) to a reaction with an imino-halogenating agent and then with an imino-etherifing agent, if necessary, followed by hydrolysis. Acid hydrolysis is one of the conventional methods for removing the amino-protecting groups and is applicable to the removal of such groups as an alkoxycarbonyl group, formyl group and trityl group. The acids available for this acid hydrolysis may be formic acid, trifluoroacetic acid, p-toluenesulfonic acid, hydrochloric acid and other organic or inorganic acids, and preferably the acids are formic acid, trifluoroacetic acid and hydrochloric acid which afford easy after-treatment of the reaction mixture. These acids for hydrolysis are selected properly according to the nature of the amino-protecting group to be removed. This hydrolysis reaction may be carried out either in the absence of any solvent or in the presence of a solvent such as water, a hydrophilic organic solvent or a mixture of organic solvents. When trifluoroacetic acid is employed for the acid hydrolysis, the reaction may suitably be conducted in the presence of anisole.

The carboxyl-protecting group may be removed also in a conventional manner, for example, by hydrolysis or reduction. Acid hydrolysis is one of the conventional deprotection methods which is advantageously applicable to the removal of the carboxyl-protecting group of such kind as silyl group and diphenylmethyl group.

The conversion of the carboxyl group into the metabolically unstable ester group may be performed by a conventional method comprising reacting a metal salt of the corresponding carboxylic acid compound with an alkyl halide such as a pivaloyloxymethyl halide e.g. chloride in an organic solvent.

Method 2:

According to this Method 2, such a cephalosporin compound of the formula (I) where the group A denotes a 3-lower-alkylthiazolyl group, that is, such a compound of the following formula (I'):

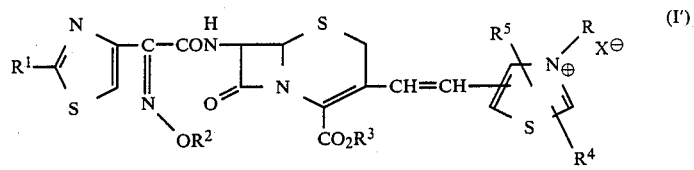

wherein $R^1$, $R^2$ and $R^3$ are as defined above, R is a lower alkyl group, and $R^4$ and $R^5$ are the same or different and each are a hydrogen atom, a lower alkyl group or a halogen atom such as chlorine atom (which may be prepared by the procedure of the Method 1 above) is produced by the method comprising reacting a compound of the formula (I'')

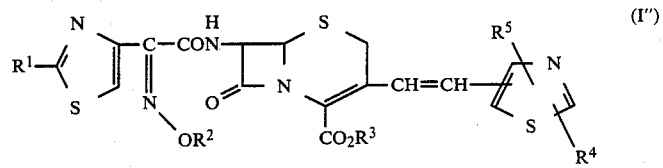

wherein $R^1$, $R^2$, $R^3$, $R^4$ and $R^5$ are as defined above, with an alkylating agent selected from an alkyl halide of the formula RX wherein R is a lwer alkyl group such as methyl and ethyl and X is a halogen atom such as chlorine, bromine or iodine atom; a mono- or di-lower-alkyl sulfate; and a lower alkyl lower-alkanesulfonate, to alkylate the 3-nitrogen atom of the thiazolyl group of the compound of the formula (I''). The alkyl halide of the formula RX as the alkylation agent may be methyl bromide, methyl iodide, ethyl bromide and ethyl iodide, for example. The mono-or di-lower-alkyl sulfate as the alkylation agent may be mono-methyl or di-methyl sulfate and mono-ethyl or di-ethyl sulfate. The lower alkyl lower-alkanesulfonate may be methyl methanesulfonate, for example. The reaction of alkylating the 3-nitrogen atom of the thiazolyl group of the compound (I'') may be achieved in a conventional manner known for alkylation of the organic nitrogen atom. When the alkylation reaction is conducted using a lower alkyl ester of the sulfuric or sulfonic acid as the alkylating agent (RX), this reaction may normally be conducted in a solvent such as benzene, toluene, dichloroethane, dichloromethane, chloroform, water, acetone, tetrahydrofurane, ethanol, ethyl ether, dimethylformamide or in any other solvent which exerts no adverse effect on the progress of this reaction.

This reaction according to Method 2 may also preferably be conducted in the presence of such an inorganic or organic base as described in Method 1. The alkylation reaction as above may be carried out at any temperature which is not limited critically, and the alkylation may usually be conducted at a temperature of up to the boiling point of the solvent used in this reaction, under cooling or heating.

The product compound (I') which has been prepared by the above alkylation reaction may, if desired, then be subjected to further conventional step(s) for removing the remaining carboxyl-protecting group and/or the remaining amino-protecting group therefrom, and/or to further convention step(s) for converting the carboxyl group(s) of the product compound (I') into a metabolically unstable, non-toxic ester (carboxylate) group, in the same manner as described for the procedures of Method 1.

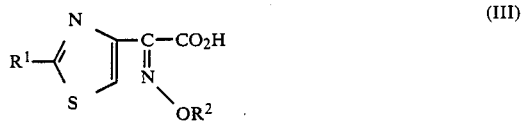

wherein $R^1$ and $R^2$ are as defined above, or a functional equivalent thereof (including a reactive acid derivative of the compound of the formula (III)) in an unreactive solvent at a temperature of not higher than the boiling temperature of the solvent used, to produce the compound of the formula (I), and then, if desired, where the product compound of the formula (I) as produced is such one as shown by the formula (I'')

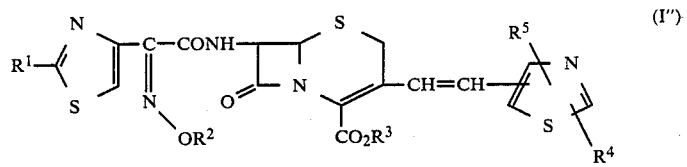

According to a second aspect of this invention, therefore, there is provided a process for the production of a cephalosporin compound of the general formula (I)

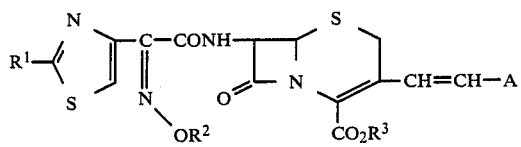

wherein $R^1$, $R^2$ and $R^3$ are as defined above, and $R^4$ and $R^5$ are the same or different and each are a hydrogen atom, a lower alkyl group or a halogen atom such as a chlorine atom, alkylating the 3-nitrogen atom of the thiazolyl group of the compound of the formula (I'') by reacting with an alkyl halide of the formula RX wherein R is a lower alkyl group and X is a halogen atom, such as chlorine or bromine atom, or a mono- or di-loweralkyl sulfate or a lower alkyl lower-alkanesulfonate, to produce the compound of the formula (I''')

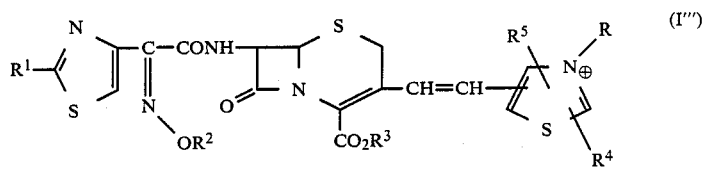

wherein $R^1$ is an amino group or a protected amino group, $R^2$ is a lower alkyl group, a carboxymethyl group or a protected carboxymethyl group, $R^3$ is a hydrogen atom, a salt-forming cation or a carboxyl-protecting group, and A is an unsubstituted or substituted phenyl group, an unsubstituted or substituted furyl group or an unsubstituted or substituted thiazolyl group or an unsubstituted or substituted 3-lower-alkylthiazolio group, characterized in that the process comprises reacting a 7-aminocephalosporanic acid compound of the general formula (II)

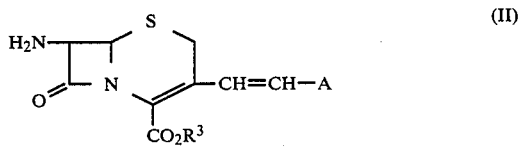

wherein $R^3$ and A are as defined above, or a functional equivalent thereof (including a reactive derivative at the amino group of the compound of the formula (II) and a salt of the compound of the formula (II)), with a 2-(2-aminothiazol-4-yl)-2-alkoxyimino-acetic acid compound of the formula (III)

wherein $R^1$, $R^2$, $R^3$, $R^4$ and $R^5$ are as defined above and R is corresponding to the lower alkyl group of the alkyl halide or the mono- or di-lower-alkyl sulfate or the lower alkyl lower-alkanesulfonate employed, and further, if desired, removing the remaining amino-protecting group and the remaining carboxyl-protecting group from the product compound of the formula (I) or of the formula (I''').

The process of the second aspect of this invention may include a further step of reacting the compound of the formula (I) where $R^3$ is a hydrogen atom, with an alkali metal hydroxide, an alkali metal hydrogen carbonate or an alkali metal carbonate or an alcohol such as a lower alkanol to produce the compound of the formula (I) where $R^3$ is an alkali metal cation or an ester-forming group such as a lower alkyl group. This reaction may be carried out in a known manner for the conversion of a carboxylic acid into a corresponding alkali metal carboxylate or an ester of the carboxylic acid. In this way, the compound of the formula (I) in the form of a free carboxylic acid may be converted into the form of an alkali metal carboxylate or a carboxylic acid ester.

Examples of the pharmaceutically acceptable salts of the compound of the formula (I) include ordinary non-toxic salts, for example, salts (carboxylate) with an alkali metal such as sodium and potassium; salts with an alkaline earth metal such as calcium and magnesium; ammonium salt; acid addition salts of the compound (I) with an organic base such as trimethylamine, triethylamine, pyridine, picoline, dicyclohexylamine, N,N'-dibenzylethylenediamine; acid-addition salts of the compound (I) with an organic acid such as acetic acid, trifluoroacetic acid, maleic acid, tartaric acid, methanesulfonic acid, benzenesulfonic acid, formic acid and toluenesulfonic acid; acid-addition salts with an inorganic acid such as hydrochloric acid, hydrobromic acid, sulfuric acid and phosphoric acid; acid-addition salts with an amino acid such as arginic acid, aspartic acid and glutamic acid.

Examples of the pharmaceutically acceptable ester of the compound of the formula (I) according to this invention include the esters which are obtained by the esterification of the 2-carboxyl group of the compound of the formula (I) with a lower alkanoyloxymethyl group such as pivaloyloxymethyl group, a lower alkylcarbonyloxyalkyl group, a lower alkoxycarbonyloxyalkyl group, or a (2-oxo-1,3-dioxolene-4-yl)methyl group and the like.

The compounds of this invention are all novel compounds. Minimum inhibitory concentrations (MIC., $\mu$g/ml) of some of the new compounds against growth of bacteria as determined by agar-dilution method are shown in Table 1 below. As be apparent from Table 1, all the compounds under test of this invention exhibit high antibacterial activity and a wide range of antibacterial spectra, indicating that the new compounds of this invention are useful as antibacterial agent.

7-[2-methoxyimino-2-(2-aminothiazol-4-yl)acetamido]-3-[2-(2-furyl)vinyl]-3-cephem-4-carboxylic acid sodium salt (cyn-isomer, cis-isomer).

Example No. 13 Compound:
7-[2-methoxyimino-2-(2-aminothiazol-4-yl)acetamido]-3-[2-(5-nitor-2-furyl)vinyl]-3-cephem-4-carboxylic acid sodium salt (syn-isomer, trans-isomer).

Example No. 14 Compound:
7-[2-methoxyimino-2-(2-aminothiazol-4-yl)acetamido]-3-[2-(o-fluorophenyl)vinyl]-3-cephem-4-carboxylic acid trifluoroacetate (syn-isomer, mixed cis- and trans-isomers).

Example No. 15 Compound:
7-[2-methoxyimino-2-(2-aminothiazol-4-yl)acetamido]-3-[2-(3,4-dimethyl-5-thiazolio)vinyl]-3-cephem-4-carboxylic acid di-trifluoroacetate (syn-isomer).

Example No. 16 Compound:
7-[2-carboxymethoxyimino-2-(2-aminothiazol-4-yl)acetamido]-3-[2-(4-methylthiazol-5yl)vinyl]-3-cephem-4-carboxylic acid trifluoroacetate (syn-isomer, trans-isomer).

Example No. 18 Compound:
7-[2-methoxyimino-2-(2-aminothiazol-4-yl)acetamido-3-[2-(4-methylthiazol-5-yl)vinyl]-3cephem-4-carboxylic acid sodium salt (syn-isomer, trans-isomer).

Example No. 21 Compound:
7-[2-methoxyimino-2-(2-aminothiazol-4-yl)acetamido]-3-[2-(4-chlorothazol-5-yl)vinyl]-3-cephem-4-carboxylic acid sodium salt (syn-isomer, cis-isomer).

Example No. 30 Compound:
7-[2-methoxyimino-2-(2-aminothiazol-4-yl)acetamido]-3-[2-(2-methylthiazol-5-yl)vinyl]-3-cephem-4-carboxylic acid trifluoroacetate (syn-isomer, trans-isomer).

TABLE 1

| Test Organisms | MIC. ($\mu$g/ml) Example No. Compound | | | | | | | | | | | | | |
|---|---|---|---|---|---|---|---|---|---|---|---|---|---|---|
| | 10 | 11 | 12 | 13 | 14 | 15 | 16 | 18 | 21 | 30 | 31 | 32 | 33 | 34 |
| Staphylococcus aureus 209P JC-1 | 0.20 | 0.78 | 0.39 | 6.25 | 0.20 | 0.78 | 3.13 | 0.39 | 0.10 | 0.78 | 0.78 | 0.39 | 0.39 | 0.20 |
| Staphylococcus aureus Smith | 0.39 | 0.78 | 0.78 | 6.25 | 0.39 | 0.78 | 3.13 | 0.39 | 0.20 | 1.56 | 1.56 | 0.78 | 0.39 | 0.20 |
| Escherichia coli NIHJ JC-2 | 0.39 | 3.13 | 3.13 | 6.25 | 3.13 | 0.10 | 0.39 | 0.78 | 0.20 | 0.78 | 1.56 | 1.56 | 0.39 | 3.13 |
| Klebsiella pneumoniae PCI 602 | 0.39 | 3.13 | 1.56 | 3.13 | 3.13 | 0.10 | 0.20 | 0.39 | 0.10 | 0.78 | 1.56 | 1.56 | 0.20 | 3.13 |
| Proteus mirabilis GN 79 | 0.39 | 0.78 | 0.78 | 12.5 | 0.20 | 0.78 | 0.05 | — | 0.20 | 0.20 | 0.78 | — | 0.39 | 0.78 |
| Proteus vulgaris GN 76 | 0.20 | 0.78 | 0.39 | 3.13 | 0.20 | 0.39 | ≦0.025 | 0.10 | 0.10 | 0.10 | 0.20 | 0.10 | 0.10 | 1.56 |
| Proteus rettgeri GN 624 | 3.13 | 3.13 | 3.13 | 3.13 | 1.56 | 0.39 | 1.56 | 0.39 | 1.56 | 0.20 | 0.78 | 6.25 | 0.78 | 1.56 |
| Salmonella typhimurium LT-2 | 0.39 | 6.25 | 1.56 | 6.25 | 3.13 | 0.10 | 0.10 | 0.78 | 0.20 | 0.39 | 1.56 | 0.78 | 0.39 | 3.13 |
| Serratia marcescens No. 1 | 0.39 | 1.56 | 1.56 | 6.25 | 1.56 | 0.10 | 0.05 | 0.39 | 0.20 | 0.20 | 0.78 | 0.78 | 0.39 | 1.56 |
| Pseudomonas aeruginosa MB 3833 | 25 | >50 | >50 | >50 | >50 | >50 | 12.5 | 50 | 12.5 | >50 | >50 | 100 | 25 | 100 |

Referring to Table 1 above, the Compounds of Examples under test are identified as follows:

Example No. 10 Compound:
7-[2-methoxyimino-2-(2-aminothiazol-4-yl)acetamido]-3-[2-(4-methylthiazol-5-yl)vinyl]-3-cephem-4-carboxylic acid trifluoroacetate (cyn-isomer, cis-isomer)

Example No. 11 Compound:
7-[2-methoxyimino-2-(2-aminothiazol-4-yl)acetamido]-3-(2-phenylvinyl)-3-cephem-4-carboxylic acid trifluoroacetate (cyn-isomer, cis-isomer)

Example No. 12 Compound:

mer).

Example No. 31 Compound:
7-[2-methoxyimino-2-(2-aminothiazol-4-yl)acetamido]-3-[2-(2-methylthiazol-5-yl)vinyl]-3-cephem-4-carboxylic acid trifluoroacetate (syn-isomer, cis-isomer).

Example No. 32 Compound:
7-[2-methoxyimino-2-(2-aminothiazol-4-yl)acetamido]-3-[2-(thiazol-4-yl)vinyl]-3-cephem-4-carboxylic acid sodium salt (syn-isomer, cis-isomer).

Example No. 33 Compound:

7-[2-methoxyimino-2-(2-aminothiazol-4-yl)acetamido]-3-[2-(thiazol-5-yl)vinyl]-3-cephem-4-carboxylic acid sodium salt (syn-isomer, cis-isomer).

Example No. 34 Compound:
7-[2-methoxyimino-2-(2-aminothiazol-4-yl)acetamido]-3-[2-(2,4-dichlorothiazol-5-yl)vinyl]-3-cephem-4-carboxylic acid sodium salt (syn-isomer, cis-isomer).

The new compound of the formula (I) or the formula (Ia) to (If) according to this invention, or a pharmaceutically acceptable salt or ester thereof may be formulated into a pharmaceutical composition by mixing with a pharmaceutically acceptable solid or liquid carrier or vehicle when it is to be administered to man for the therapeutic treatment of bacterial infections.

According to a further aspect of this invention, therefore, there is provided a pharmaceutical, antibacterial composition which comprises an antibacterially effective amount of the compound of the fromula (I) or of the formula (Ia) to (If) as defined hereinbefore or a pharmaceutically acceptable salt or ester thereof as the active ingredient, in combination of a pharmaceutically acceptable carrier for the active ingredient.

The pharmaceutically acceptable carrier as mixed with the active ingredient compound may be an ordinary solid or liquid one, either organic or inorganic, which may be chosen appropriately depending on whether the pharmaceutical formulation as prepared is to be administered orally or non-orally or applied externally. The pharmaceutical composition of this invention may be of any conventional formulation form such as capsules, tablets, sugar-coated pills, ointment, suppository, solution, suspension and emulsion. Other conventional additives, including adjuvant, stabilizing agent, wetting agent, emulsifying agent, buffer solution may also be incorporated into the pharmaceutical composition of this invention containing the compound (I) as the active ingredient.

The new cephalosporin compound of this invention as orally administered is easily absorbed through the intestines by a living animal and maintains its antibacterial activity to a substantial extent in the body of the animal until it is excreted in the urine of the animal, and this may be observed by determining the remaining amount of the cephalosporin compound of this invention which can be recovered in the urine without receiving a substantial degradation of the compound in vivo. Some tests were made to evaluate the amount of the cephalosporin compound of this invention which can be recovered as the antibacterially active compound from the urine after it was orally given to mice.

Test 1

To mice of ICR-strain (male, 4-weeks-aged, three in each group) was orally administered the compound under test identified below, at a dosage of the compound of 0.5 mg per mouse. The compound under test was given as a suspension of the test compound in a solution of 0.2% carboxymethylcellulose (CMC) in water. By the end of 4 hours after the administration of the test compound, all the amounts of the urine excreted by the treated mice were collected together, and the total quantity of the cephalosporin compound of this invention (as the free carboxylic acid form) in the urine was determined according to a paper-disc assay method using *Escherichia coli* K-12 8236 as the assaying strain.

The compound under test was the Example No. 22 Compound, namely 7-[2-methoxyimino-2-(2-aminothiazol-4-yl)acetamido-3-[2-(4-chlorothiazol-5-yl)vinyl]-3-cephem-4-carboxylic acid (syn-isomer, cis-isomer) pivaloyloxymethyl ester; and the Example No. 38 Compound, namely 7-[2-methoxyimino-2-(2-aminothiazol-4-yl)acetoamido]-3-[2-(thiazol-5-yl)vinyl]-3-cephem-4-carboxylic acid (cyn-isomer, cis-isomer) pivaloyloxymethyl ester.

Rate of recovery of the cephalosporin compound in urine was calculated in term of percentages of the molar quantity of the cephalosporin compound as recovered (as the free carboxylic acid form) based on the molar quanitity of the cephalosporin compound as orally given.

The test results obtained (as averaged for three mice) are shown in Table 2 below.

TABLE 2

| Test compound | Rate of recovery of the test compound in urine (%) |
|---|---|
| Example No. 22 Compound | 24 |
| Example No. 38 Compound | 20 |

In the above tests, the cephalosporin compounds under test as orally given each were converted in vivo into the corresponding free carboxylic acid form owing to easy cleavage of the ester-forming pivaloyloxymethyl group from the 4-carboxyl group of the compound after they were absorbed in the animal body. The test compounds were excreted in the urine in the form of its free carboxylic acid, of which the antibacterial potency was evaluated by the bio-assay method.

This invention is now illustrated with reference to the following Examples. Examples 1–39 illustrate the procedures for preparing the new cephalosporin compounds of this invention, and Reference Examples 1–8 illustrate the procedures for preparing the starting compounds employed for the preparation of the new compounds of this invention.

REFERENCE EXAMPLE 1

Production of 7-(phenoxyacetamido)-3-[2-(4-methylthiazol-5-yl)vinyl]-3-cephem-4-carboxylic acid benzhydryl ester (1) Benzhydryl 7-(phenoxyacetamido)-3-(triphenylphosphoran-diylmethyl)-3-cephem-4-carboxylate (1.55 g ) and 4-methylthiazol-5-carboaldehyde (0.305 g) were dissolved in methylene chloride (20 ml), to which aqueous saturated sodium bicarbonate (20 ml) was added at ambient temperature. The resultant mixture was stirred for 17 hours at ambient temperature. The mixture was allowed to stand until it separated into the aqueous phase and organic solvent phase. The aqueous phase was removed and washed with methylene chloride (20 ml), and the washings (in methylene chloride) were combined with the organic solvent phase separated. The combined solution was dried over anhydrous magnesium sulfate and then concentrated to dryness under reduced pressure. The solid residue obtained was purified chromatographically on a column of silica gel (Wako gel C-300) (40 g) as developed with benzene-ethyl acetate (5:1) as the development solvent. The entitled compound, 7-(phenoxyacetamido)-3-[2-(4-methylthiazol-5-yl)vinyl]-3-cephem-4-carboxylic acid benzhydryl ester (0.741 g) was obtained.

NMR, δ (CDCl$_3$): 2.34 (3H, s), 3.24 (1H, d, J=18 Hz), 3.48 (1H, d, J=18 Hz), 4.55 (2H, s), 5.12 (1H, d, J=5 Hz), 5.95 (1H, dd, J=5 Hz, 9 Hz), 6.25 (1H, d,

J=12 Hz), 6.49 (1H, d, J=12 Hz), 6.8–7.5 (16H, m), 8.56 (1H, s).

(2) Benzhydryl 7-(phenoxyacetamido)-3-[2-(4-methylthiazol-5-yl)vinyl]-3-cephem-4-carboxylate (0.725 g) was dissolved in anisole (2 ml), to which trifluoroacetic acid (7 ml) was added under ice-cooling. The mixture was stirred for 1 hour under ice-cooling. The reaction mixture was concentrated under reduced pressure to give a syrup, whcih was then solidified by addition of isopropyl ether thereto. The solid obtained was pulverized and was mixed with isopropyl ether for the washing purpose, and the mixture was filtered to recover the solid which was then dried under reduced presssure. 7-(Phenoxyacetamido)-3-[2-(4-methylthiazol-5-yl)vinyl]-3-cephem-4-carboxylic acid (0.512 g) was thus obtained.

NMR, δ (CDCl$_3$): 2.38 (3H, s), 3.19 (1H, d, J=18 Hz), 3.46 (1H, d, J=18 Hz), 4.55 (2H, s) 5.09 (1H, d, J=5 Hz), 5.91 (1H, d, J=5 Hz), 6.44 (1H, d, J=12 Hz), 6.57 (1H, d, J=12 Hz), 6.8–7.6 (6H, m), 8.79 (1H, s).

(3) 7-(Phenoxyacetamido)-3-[2-(4-methylthiazol-5-yl)vinyl]-3-cephem-4-carboxylic acid (0.490 g) was dissolved in ethyl acetate (5 ml), to which sodium 2-ethylhexanoate (0.300 g) was added. The resultant mixture was stirred for 30 minutes, and the precipitate as formed was removed from the mixture by filtration and washed with a mixture of ethyl acetate and isopropyl ether (1:1). The solid product (as the sodium salt) was dissolved in dimethylformamide (5 ml) under ice-cooling, to which was added such a solution in dimethylformamide (3 ml) of iodomethyl pivalate as prepared from chloromethyl pivalate (0.450 g) and sodium iodide (0.450 g). The resultant mixture was stirred for 1 hour under ice-cooling. To the reaction mixture was added ethyl acetate (50 ml), followed by washing the mixture three times with ice-water (each 30 ml). The organic solvent phase was separated out of the mixture, dried over anhydrous magnesium sulfate and then concentrated to dryness under reduced pressure. The solid residue obtained was purified chromatographically on a column of silica gel (Wako-gel C-300) (20 g) as developed with benzene-ethyl acetate (5:1) as the development solvent. 7-(Phenoxyacetamido)-3-[2-(4-methylthiazol-5-yl)vinyl]-3-cephem-4-carboxylic acid pivaloyloxymethyl ester (0.405 g) was thus obtained.

NMR, δ (CDCl$_3$): 1.15 (9H, s), 2.45 (3H, s), 3.17 (1H, d, J=18 Hz), 3.50 (1H, d, J=18 Hz), 4.57 (2H, s), 5.12 (1H, d, J=5 Hz), 5.77 (1H, d, J=5 Hz), 5.84 (1H, d, J=5 Hz), 5.95 (1H, dd, J=5 Hz, 9 Hz), 6.35 (1H, d, J=12 Hz), 6.64 (1H, d, J=12 Hz), 6.8–7.5 (6H, m), 8.62 (1H, s).

(4) 7-(Phenoxyacetamido)-3-[2-(4-methylthiazol-5yl vinyl]-3-cephem-4-carboxylic acid pivaloyloxymethyl ester (0.303 g) was dissolved in methylene chloride (3 ml). The solution obtained was poured into a solution (10 ml) containing phosphorus pentachloride (0.331 g) and pyridine (0.43 g) in methylene chloride at −30° C. The resultant solution was stirred for 3 hours under ice-cooling and was poured into methanol (20 ml) as cooled previously to −30° C., followed by stirring the mixture for further 30 minutes at ambient temperature. The reaction solution obtainedd was then poured into a mixture of aqueous saturated sodium chloride (50 ml) and methylene chloride (50 ml) under ice-cooling, followed by stirring for 1 hour under ice-cooling. The organic phase was separated from the aqueous phase, and the aqueous phase was extracted with methylene chloride (20 ml). The extract (in methylene chloride) was combined with said organic phase, and the resultant mixture was washed with aqueous saturated sodium bicarbonate solution. The washed organic phase was dried over anhydrous magnesium sulfate and concentrated under reduced pressure to a volume of 5 ml. 7-Amino-3-[2-(4-methylthiazol-5-yl)vinyl]-3-cephem-4-carboxylic acid pivaloyloxymethyl ester was thus obtained as its solution in methylene chloride.

EXAMPLE 1

Production of 7-[2methoxyimino-2-(2-tritylaminothiazol-4-yl)acetamido]-3-[2-(4-methylthiazol-5-yl)vinyl]-3-cephem-4-carboxylic acid (syn-isomer) pivaloyloxymethyl ester

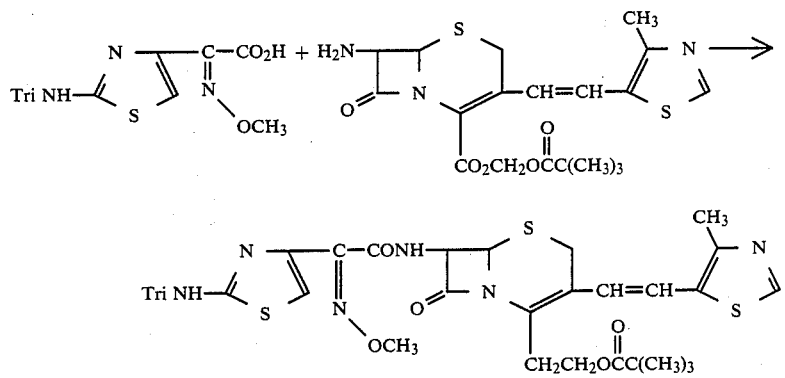

(Tri denotes trityl group.)

7-Amino-3-[2-(4-methylthiazol-5-yl)vinyl]-3-cephem-4-carboxylic acid pivaloyloxymethyl ester (0.229 g) as prepared in Reference Example 1 above was dissolved in methylene chloride (5 ml). The resultant solution was admixed with 2-(2-tritylaminothiazol-4-yl)-2-methoxyiminoacetic acid (syn-isomer) (0.235 g) and methylene chloride (5 ml). To the mixture obtained were further added pyridine (0.07 ml) and then dropwise phosphorus oxychloride (0.07 ml) at −20° C. The reaction mixture was stirred for 10 minutes at 0° C. and poured into a mixture of ice-water (50 ml) and ethyl acetate (50 ml). After stirring, the organic phase was separated from the aqueous phase and washed with ice-wated and then with ice-cooled aqueous saturated sodium hydrogen carbonate solution. The organic phase was dried over anhydrous magnesium sulfate and concentrated under reduced pressure. The residue was purified chromatographically on a column of silica gel (Wako gel C-300) (20 g) as developed with benzene-ethyl acetate (5:1) as the development solvent. 7-[2-Methoxyimino-2(2-tritylaminothiazol-4yl)acetamido]-3-[2-(4-methylthiazol-5-yl)vinyl]-3-cephem-4-carboxylic acid (syn-isomer) pivaloyloxymethyl ester (0.184 g) was obtained.

NMR, δ (CDCl$_3$): 1.13 (9H, s), 2.43 (3H, s), 3.26 (1H, d, J=18 Hz), 3.57 (1H, d, J=18 Hz), 4.04 (3H, s), 5.13 (1H, d, J=5 Hz), 5.76 (1H, d, J=5 Hz), 5.82 (1H, d, J=5 Hz), 5.95 (1H, dd, J=5 Hz, 9 Hz), 6.34 (1H, d, J=12 Hz), 6.64 (1H, d, J=12 Hz), 6.70 (1H, s), 6.90 (1H, d, J=9 Hz), 7.00 (1H, broad s), 7.1-7.5 (25H, m), 8.59 (1H, s).

EXAMPLE 2

Production of 7-[2-methoxyimino-2-(2-aminothiazol-4-yl)acetamido]-3-[2-(4-methylthiazol-5-yl)vinyl]-3-cephem-4-carboxylic acid (syn-isomer) pivaloyloxymethyl ester 7-[2-Methoxyimino-2-(2-tritylaminothiazol-4-yl)acetamido]-3-[2-(4-methylthiazol-5-yl)vinyl]-3-cephem-4-carboxylic acid (syn-isomer) pivaloyloxymethyl ester (0.160 g) was dissolved in anisole (0.5 ml). The resultant solution was admixed with trifluoroacetic acid (1.15 ml) under ice-cooling, followed by stirring for 30 minutes again under ice-cooling. The reaction solution was mixed with isopropyl ether (30 ml), and the powder substance deposited was recovered by filtration and washed with isopropyl ether. The solid obtained was dissolved in ethyl acetate (20 ml), washed with ice-coole aqueous saturated sodium hydrogen carbonate solution (10 ml). The organic phase was separated from the aqueous phase, dried over anhydrous sodium sulfate and concentrated under reduced pressure. 7-[2-Methoxyimino-2-(2-aminothiazol-4-yl)acetamido]-3-[2-(4-methylthiazol-5-yl)vinyl]-3-cephem-4-carboxylic acid (syn-isomer) pivaloyloxymethyl ester (0.083) was thus obtained.

NMR, δ (CDCl$_3$): 1.14 (9H, s), 2.44 (3H, s), 3.30 (1H, d, J=18 Hz), 3.47 (1H, d, J=18 Hz), 4.04 (3H, s), 5.17 (1H, d, J=5 Hz), 5.27 (2H, b), 5.77 (1H, d, J=5 Hz), 5.82 (1H, d, J=5 Hz), 6.03 (1H, dd, J=5 Hz, 9 Hz), 6.35 (1H, d, J=12 Hz), 6.64 (1H, d, J=12 Hz), 6.88 (1H, s), 7.35 (1H, d, J=9 Hz), 8.59 1H, s).

EXAMPLE 3

7-Amino-3-[2-(4-methylthiazol-5-yl)vinyl]-3-cephem-4-carboxylic acid benzhydryl ester (0.223 g) and 2-(2-tritylaminothiazol-4-yl)-2-methoxyiminoacetic acid (0.252 g) were reacted with each other and the reaction product was processed in the same manner as in Example 1, to obtain 7-[2-methoxyimino-2-(2-tritylaminothiazol-4-yl)acetamide]-3-[2-(4-methylthizol-5-yl)vinyl]-3-cephem-4-carboxylic acid (syn-isomer) benzhydryl ester (0.215 g).

NMR, δ (CDCl$_3$): 2.35 (3H, d, J=18 Hz), 3.45 (1H, d, J=18 Hz), 4.05 (3H, s), 5.14 (1H, d, J=5 Hz), 5.98 (1H, dd, J=5 Hz, 9 Hz), 6.27 (1H, d, J=12 Hz), 6.45 (1H, d, J=12 Hz), 6.72 (1H, s), 6.88 (1H, s), 6.99 (1H, broad s), 7.10-7.5 (26H, m), (1H, s).

EXAMPLES 4-8

The following compounds were produced in the same manner as in Example 1:

EXAMPLE 4

7-[2-Methoxyimino-2-(tritylaminothiazol-4-yl)acetamido]-3-(2-phenylvinyl)-3-cephem-4-carboxylic acid (syn-isomer) benzhydryl ester (yield 68%).

NMR, δ (CDCl$_3$): 3.25 (2H, broad s), 4.04 (3H, s), 5.05 (1H, d, J=5 Hz), 5.91 (1H, d, J=5 Hz), 6.48 (1H, d, J=12 Hz), 6.60 (1H, d, J=12 Hz), 6.74 (1H, s), 6.95 (1H, s), 7.0-7.5 C32H, m).

EXAMPLE 5

7-[2-Methoxyimino-2-(2-tritylaminothiazol-4-yl)acetamido]-3-[2-(2-furyl)vinyl]-3-cephem-4-carboxylic acid (syn-isomer) benzhydryl ester (yield 62%).

NMR, δ (CDCl$_3$): 3.50 (2H, broad s), 4.07 (3H, s), 5.11 ((1H, d, J=5 Hz), 5.91 (1H, dd, J=5 Hz, 9 Hz), 6.1-6.4 (4H, m), 6.76 (1H, s), 7.00 (1H, broad s), 7.1-7.6 (27H, m).

EXAMPLE 6

7-[2-(Methoxyimino-2-(2-tritylaminothiazol-4-yl)acetamido]-3-[2-(5-nitro-2-furyl)vinyl]-3-cephem-4-carboxylic acid (syn-isomer) benzhydryl ester (yield 75%).

NMR, δ (CDCl$_3$): 3.40 (1H, d, J=18 Hz), 3.63 (1H, d, J=18 Hz), 4.10 (3H, s), 5.32 (1H, d, J=5 Hz), 6.05 (1H, dd, J=5 Hz, 9 Hz), (1H, d, J=12 Hz), 6.31 (1H, d, J=4 Hz), 6.53 (1H, d, J=12 Hz), 6.78 (1H, s), 6.86 (1H, s), 7.00 (1H, broad s), 7.13 (1H, d, J=4 Hz), 7.15-7.5 (26H, m).

EXAMPLE 7

7-2-Methoxyimino-2-(2-tritylaminothiazol-4-yl)acetamido]-3-[2-(o-fluorophenyl)vinyl]-3-cephem-4-carboxylic acid (syn-isomer) benzhydryl ester (yield 71%).

NMR, δ (CDCl$_3$): 3.23 (2H, broad s), 4.02 (3H, s), 5.03 (1H, d, J=5 Hz), 5.91 (1H, dd, J=5 Hz, 9 Hz), 6.57 (1H, d, J=12 Hz), 6.63 (1H, d, J=12 Hz), 6.72 (1H, s), 6.93 (1H, s), 6.95-7.5 (31H, n).

EXAMPLE 8

7-[2-t-Butoxycarbonylmethoxyimino-2-(2-tritylaminothiazol-4-yl)acetamido]-3-[2-(4-methylthiazol-5-yl)vinyl]-3-cephem-4-carboxylic acid (syn-isomer) benzhydryl ester (yiled 81%).

NMR, δ (CDCl$_3$): 1.43 (9H, s) 2.36 (3H, s), 3.25 (1H, d, J=18 Hz), 3.55 (1H, d, J=18 Hz), 4.75 (2H, S), 5.14 (1H, d, J=5 Hz), 5.94 (1H, dd, J=5 Hz, 9 Hz), 6.27 (1H, d, J=12 Hz), 6.45 (1H, d, J=12 Hz), 6.80 (1H, s), 6.86 (1H, s), 6.99 (1H, broad s), 7.1-7.5 (25H, m), 8.53 (1H, s), 8.56 (1H, d, J=9 Hz).

EXAMPLE 9

Production of 7-[2-methoxyimino-2-(2-tritylaminothiazol-4-yl)acetamido]-3-[2-(3,4-dimethyl-5-thiazolio)vinyl]-3-cephem-4-carboxylic acid (syn-isomer) benzhydryl ester iodide 7-[2-Methoxyimino-2-tritylaminothiazol-4-yl)acetamido]-3-[2-(4-methylthiazol-5-yl)vinyl]-3-cephem-4-carboxylic acid benzhydroyl ester (0.164 mg) was dissolved in benzene (5 ml), to which was added methyl iodide (1 ml). The solution so obtained was stirred for 7 days so that a precipitate was deposited. The precipitate was removed by filtration, washed with benzene and dried under reduced pressure, to afford 7-[2-methoxyimino-2-(2-tritylaminothiazol-4-yl)acetamido]-3-[2-(3,4-dimethyl-5-thiazolio)vinyl]-3-cephem-4-carboxylic acid (syn-isomer) benzhydryl ester iodide (0.122 mg).

NMR, δ (CDCl$_3$): 2.30 (3H, s), 3.32 (1H, d, J=18 Hz), 3.65 (1H, d, J=18 Hz), 4.02 (3H, s), 4.06 (3H, s), 5.42 (1H, d, J=5 Hz), 5.92 (1H, dd, J=5 Hz, 9 Hz), 6.29 (1H, d, J=12 Hz), 6.56 (1H, d, J=12 Hz), 6.64 (1H, s), 6.89 (1H, s), 7.0–7.5 (27H, m) 10.19 (1H, s).

EXAMPLE 10

Production of 7-[2-methoxyimino-2-(2-aminothiazol-4-yl)acetamido]-3-[2-(4-methylthiazol-5-yl)vinyl]-3-cephem-4-carboxylic acid (syn-isomer, cis-isomer) trifluoroacetate 7-[2-Methoxyimino-2-(2-tritylaminothiazol-4-yl)acetamido]-3-[2-(4-methylthiazol-5-yl)vinyl]-3-cephem-4-carboxylic acid benzhydryl ester (0.11 g) was dissolved in anisole (0.33 mg), to which was added trifluoroacetic acid (1.1 ml) under ice-cooling. The solution so obtained was stirred for 1 hour under ice-cooling and the reaction solution was admixed with isopropyl ether (30 ml) to deposit a precipitate. The precipitate was recovered by filtration, washed with isopropyl ether and dried under reduced pressure. 7-[2-Methoxyimino-2-(2-aminothiazol-4-yl)acetamido]-3-[2-(4-methylthiazol-5-yl)vinyl]-3-cephem-4-carboxylic acid (syn-isomer) trifluoroacetate (0.067 g) was obtained.

NMR, δ (CD$_3$SOCD$_3$): 2.44 (3H, s), 3.39 (1H, d, J=18 Hz), 3.46 (1H, d, J=18 Hz), 3.84 (3H, s), 5.22 (1H, d, J=5 Hz), 5.80 (1H, dd, J=5 Hz, 9 Hz), 6.36 (1H, d, J=12 Hz), 6.67 (1H, d, J=12 Hz), 6.76 (1H, s), 8.90 (1H, s), 9.63 (1H, d, J=9 Hz).

EXAMPLE 11–16

The following compounds were prepared in the same manner as in Example 10.

Sodium salt of the compounds of Examples 12 and 13 given below were produced by preparing the trifluoroacetate of the corresponding compounds in the same manner as in Example 10, dissolving said trifluoroacetate in an aqueous solution of 2 molar equivalents of sodium hydrogen carbonate, purifying chromatographically the resulting solution on a column of Diaion HP20 (100-fold volume) as eluted with water and aqueous 20% acetone, and freeze-drying the eluate containing the desired compound.

EXAMPLE 11

7-[2-Methoxyimino-2-aminothiazol-4-yl)acetamido]-3-(2-phenylvinyl)-3-cephem-4-carboxylic acid (syn-isomer, cis-isomer) trifluoroacetate (yield 79%).

NMR, δ (CD$_3$DOCD$_3$): 3.17 (1H, d, J=18 Hz), 3.42 (1H, d, J=18 Hz), 3.82 (3H, s), 5.20 (1H, d, J=5 Hz), 5.76 (1H, dd, J=5 Hz, 9 Hz), 6.52 (1H, d, J=12 Hz), 6.58 (1H, d, J=12 Hz), 6.73 (1H, s), 7.1–7.5 (5H, m), 9.57 (1H, d, J=9 Hz).

EXAMPLE 12

7-[2-Methoxyimino-2-(2-aminothiazol-4-yl)acetamido]-3-[2-(2-furyl)vinyl]-3-cephem-4-carboxylic acid (syn-isomer, cis-isomer) sodium salt (yield 13%).

NMR, δ (D$_2$O): 3.51 (1H, d, J=18 Hz), 3.72 (1H, d, J=18 Hz), 4.03 (3H, s), 5.39 (1H, d, J=5 Hz), 5.86 (1H, d, J=5 Hz), 6.22 (1H, d, J=12 Hz), 6.44 (1H, d, J=12 Hz), 6.4–6.6 (2H, m), 7.07 (1H, s) 7.54 (1H, d, J=2 Hz).

EXAMPLE 13

7-[2-Methoxyimino-2-(2-aminothiazol-4-yl)acetamido]-3-[2-(5-nitor-2-furyl)vinyl]-3-cephem-4-carboxylic acid (syn-isomer, trans-isomer) sodium salt (yield 53%).

NMR, δ (D$_2$O): 3.57 (1H, d, J=18 Hz), 3.82 (1H, d, J=18 Hz), 4.03 (3H, s), 5.34 (1H, d, J=5 Hz), 5.88 (1H, d, J=5 Hz), 6.76 (1H, d, J=15 Hz), 6.79 (1H, d, J=4 Hz), 7.05 (1H, s) 7.46 (1H, d, J=15 Hz), 7.60 (1H, d, J=4 Hz).

EXAMPLE 14

7-[2-Methoxyimino-2-(2-aminothiazol-4-yl)acetamido]-3-[2-(o-fluorophenyl)vinyl]-3-cephem-4-carboxylic acid (syn-isomer, mixed cis- and trans-isomers) trifluoroacetate (yield 84%).

NMR, δ (CD$_3$SOCD$_3$): 3.12 (1H, d, J=18 Hz), 3.33 (1H, d, J=18 Hz), 3.77 (3H, s), 5.07 (1H, d, J=5 Hz), 5.65 (1H, dd, J=5 Hz, 9 Hz), 6.47 (2H, s), 6.63 (1H, s), 6.9–7.5 (4H, m), 9.42 (1H, d, J=9 Hz).

EXAMPLE 15

7[2-Methoxyimino-2-(2-aminothiazol-4-yl)acetamido-3-[2-(3,4-dimethyl-5-thiazolio)vinyl]-3-cephem-4-carboxylic acid (syn-isomer) di-trifluoroacetate (yield 73%).

NMR, δ (CH$_3$SOCD$_3$): 2.42 (3H, s), 3.37 (1H, d, J=18 Hz), 3.52 (1H, d, J=18 Hz), 3.82 (3H, s), 4.04 (3H, s), 5.24 (d, J=5 Hz), 5.80 (1H, dd, J=5 Hz, 9 Hz), 6.72 (3H, s), 9.56 (1H, d, J=9 Hz), 10.25 (1H, s).

EXAMPLE 16

7-[2-Carboxymethoxyimino-2-(2-aminothiazol-4-yl)acetamido]-3-[2-(4-methylthiazol)-5-yl)vinyl]-3-cephem-4-carboxylic acid (syn-isomer, trans-isomer) trifluoroacetate (yield 58%).

NMR, δ (CD$_3$SOCD$_3$): 2.37 (3H, s), 3.36 (1H, d, J=18 Hz), 3.51 (1H, d, J=18 Hz), 4.62 (2H, s), 5.27 (1H, d, J=5 Hz), 5.87 (1H, dd, J=5 Hz, 9 Hz), 6.37 (1H, d, J=12 Hz), 6.83 (1H, s), 8.93 (1H, s), 9.62 (1H, d, J=9 Hz).

REFERENCE EXAMPLE 2

Production of 7-amino-3-[2-(4-methylthiazol-5-yl)vinyl]-3-cephem-4-carboxylic acid (trans-isomer) p-methoxybenzyl ester (1) p-Methoxybenzyl 7-phenylacetamido-3-chloromethyl-3-cephem-3-carboxylate (10.00 g, 20.52 mmol) and triphenylphosphine (5.65 g, 21.5 mmol) were dissolved in acetone (200 ml), to which sodium iodide (3.23 g, 21.5 mmol) was added at ambient temperature. The resultant mixture was stirred for 2 hours and concentrated to dryness under reduced pressure. To the solid residue were added methylene chloride (100 ml), 4-methylthiazol-5-yl-carboaldehyde

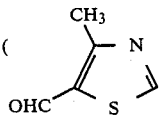

(26.07 g, 20.5 mmol) and aqueous saturated sodium hydrogen carbonate solution (100 ml) successively, followed by stirring the resultant mixture for 16 hours at ambient temperature. The mixture obtained was allowed to stand until it separated into the aqueous phase and organic solvent phase. The organic phase was separated from the aqueous phase, and washed with aqueous 10% sodium bisulfite solution (250 ml) and then with aqueous saturated sodium chloride solution (250 ml). The organic phase as washed was dried over anhydrous magnesium sulfate and then concentrated under reduced pressure. To the residue was added methanol (200 ml) to deposit a precipitate which was then filtered out, washed with methanol and dried under reduced pressure. 7-Phenylacetamido-3-[2-(4-methylthiazol-5-yl)vinyl]-3-cephem-4-carboxylic acid (trans-isomer) p-methoxybenzyl ester was thus obtained as a light yellow colored powder (yield 1.20 g, 10%).

NMR, $\delta$ (CDCl$_3$): 2.40 (3H, s), 3.60 (2H, broad s), 3.62 (2H, s), 3.78 (3H, s), 4.93 (1H, d, J=5 Hz), 5.20 (2H, s), 5.79 (dd, J=5 Hz, 9 Hz), 6.6–6.9 (4H, m), 7.0–7.4 (8H, m), 8.51 (1H, s).

(2) p-Methoxybenzyl 7-phenylacetamido-3-[2-(4-methylthiazol-5-yl)vinyl]-3-cephem-4-carboxylate (trans-isomer) (0.720 g, 1.28 mmol) was dissolved in methylene chloride (3 ml). The resultant solution was poured into a solution of phosphorus pentachloride (0.800 g, 3.84 mmol) and pyridine (1.04 ml, 12.8 mmol) in methylene chloride (20 ml) at −30° C. The resultant solution was stirred for 3 hours under ice-cooling and poured into methanol (20 ml) as pre-cooled to −30° C., followed by stirring the mixture for 1 hour at ambient temperature. The reaction solution obtained was poured into a mixture of aqueous saturated sodium chloride solution (20 ml) and methylene chloride (20 ml), and the resulting mixture was stirred for 1 hour. The mixture was cooled to stand until it separated into the aqueous phase and organic solvent phase. The aqueous phase separated out was extracted with methylene chloride (20 ml) and the methylene chloride extract was combined with the organic phase mentioned above. The combined organic phase was washed with aqueous saturated sodium hydrogen carbonate solution, dried over anhydrous magnesium sulfate and concentrated under reduced pressure. The residue obtained was purified chromatographically on a column of silica gel (Wako gel C-300) (20 g) as developed with benzene-ethyl acetate (3:1) as the development solvent. The titled compound, 7-amino-3-[2-(4-methylthiazol-5-yl)vinyl]-3-cephem-4-carboxylic acid (trans-isomer) p-methoxybenzyl ester (0.443 g, 78%) was obtained.

NMR, $\delta$ (CDCl$_3$): 1.83 (1H, broad s), 2.46 (1H, s), 3.63 (1H, d, J=18 Hz), 3.71 (1H, d, J=18 Hz), 3.77 (3H, s), 4.72 (1H, d, J=5 Hz), 4.94 (1H, d, J=5 Hz), 5.23 (2H, s), 6.85 (1H, d, J=16 Hz), 6.8–6.9 (2H, m), 7.22 (1H, d, J=16 Hz), 7.3–7.4 (2H, m), 8.52 (1H, s).

EXAMPLE 17

Production of
7-[2-methoxyimino-2-(2-tritylaminothiazol-4-yl)acetamido]-3-[2-(4-methylthiazol-5-yl)vinyl]-3-cephem-4-carboxylic acid p-methoxybenzyl ester
(syn-isomer, trans-isomer)

p-Methoxybenzyl 7-amino-3-[2-(4-methylthiazol-5-yl)vinyl]-3-cephem-4-carboxylate (trans-isomer) as prepared by the method of Reference Example 2 as above and 2-(tritylaminothiazol-4-yl)-2-methoxyiminoacetic acid (syn-isomer) were reacted with each other and the reaction product was processed in the same manner as in Example 1 to give the titled compound in a yield of 72%.

NMR, $\delta$ (CDCl$_3$): 2.42 (3H, s), 3.57 (1H, d, J=18 Hz), 3.67 (1H, d, J=18 Hz), 3.73 (3H, s), 4.02 (3H, s), 5.01 (1H, d, J=5 Hz), 5.17 (2H, s), 5.84 (1H, dd, J=5 Hz, 9 Hz), 6.63 (1H, s), 6.83 (1H, d, J=16 Hz), 6.8–7.5 (20H, m), 8.49 (1H, s).

EXAMPLE 18

Production of
7-[2-methoxyimino-2-(2-aminothiazol-4-yl)acetamido]-3-[2-(4-methylthiazol-5-yl)vinyl]-3-cephem-4-carboxylic acid
sodium salt (syn-isomer, trans-isomer)

p-Methoxybenzyl 7-[2-methoxyimino-2-(2-tritylaminothiazol-4-yl)acetamido]-3-[2-(4-methylthiazol-5-yl)vinyl]-3-cephem-4-carboxylate (syn-isomer, trans-isomer) was treated with trifluoroacetic acid and processed in the same manner as in Example 10 to give a trifluoroacetate of the entitled compound (as the carboxylic acid). This trifluoroacetate obtained was dissolved in aqueous sodium hydrogen carbonate solution for neutralization and then purified chromatographically on a column of Diaion HP20 (100 fold-volume) as eluted with water and aqueous 20% acetone. The eluate containing the titled compound was lyophilized to afford the titled compound in a yield of 82%.

NMR, $\delta$ (D$_2$O): 2.50 (3H, s), 3.86 (2H, broad s), 4.06 (3H, s), 5.34 (1H, d, J=5 Hz), 5.87 (1H, d, J=5 Hz), 6.97 (1H, d, J=16 Hz), 7.06 (1H, d, J=16 Hz), 7.08 (1H, s), 8.77 (1H, s).

EXAMPLE 19

Production of
7-[2-methoxyimino-2-(2-aminothiazol-4-yl)acetamido]-3-[2-(4-methylthiazol-5-yl)vinyl]-3-cephem-4-carboxylic acid pivaloyloxymethyl ester (syn-isomer,
trans-isomer)

7-[2-Methoxyimino-2-(2-aminothiazol-4-yl)acetamido]-3-[2-(4-methylthiazol-5-yl)vinyl]-3-cephem-4-carboxylic acid sodium salt (syn-isomer, trans-isomer) (0.03 g, 0.06 mmol) was dissolved in dimethylformamide (3 ml). To the resultant solution was added a solution in dimethylformamide (1 ml) of iodomethyl pivalate (as prepared by reacting chloromethyl pivalate (0.090 g, 0.60 mmol) with sodium iodide (0.090 g, 0.06 mmol) in acetone) under ice-cooling, followed by stirring the resultant mixture for 10 minutes. The reaction solution as obtained were admixed with ice-water (20 ml) and ethyl acetate (20 ml), stirred thoroughly and then allowed to stand until the mixture separated into aqueous phase and organic phase. The organic phase was separated from the aqueous phase and washed twice with water (10 ml) and then with aqueous saturated NaCl solution (10 ml). The organic phase as washed was subsequently dried over anhydrous magnesium sulfate and concentrated under reduced pressure. The residue was purified chromatographically on a column of silica-gel (Wako-gel C-300) (5 g) as developed with ethyl acetate. The titled compound was thus obtained (yield 0.025 g, 67%).

NMR, $\delta$ (CDCl$_3$): 1.21 (9H, s), 2.48 (3H, s), 3.68 (1H, d, J=18 Hz), 3.78 (1H, d, J=18 Hz), 4.04 (3H, s), 5.12 (1H, d, J=5 Hz), 5.89 (2H, s), 5.97 (1H, dd, J=5 Hz, 9 Hz), 6.86 (1H, s), 6.98 (1H, d, J=16 Hz), 7.33 (1H, d, J=16 Hz), 7.52 (1H, d, J=9 Hz), 8.57 (1H, s).

REFERENCE EXAMPLE 3

Production of 4-chloro-thiazol-5-yl-carboaldehyde of the formula

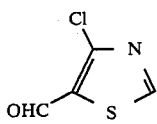

Phosphorus oxychloride (122.7 g) was added dropwise to dimethylformamide (73.1 g) under ice-cooling, and the mixture obtained was stirred for 30 minutes (for preparation of Vilsmeier reagent). The mixture was then admixed with thiazoline-2,4-dione

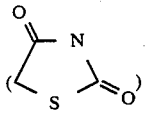

(23.4 g), followed by heating at 100° C. for 3 hours. The reaction solution was cooled to ambient temperature, poured onto ice (200 g), neutralized by addition of sodium acetate and then extracted 4 times with 200 ml-portions of methylene chloride. The resultant extract in methylene chloride was washed with a small volume of saturated aqueous sodium hydrogen carbonate solution, dried over anhydrous magnesium sulfate and concentrated under reduced pressure. The residue obtained was purified chromatographically on a column of silica gel as developed with benzene-ethyl acetate (10:1) as eluent. The titled compound (1.10 g) was obtained as light yellow colored crystals.

NMR, δ (CDCl₃): 8.93 (1H, d, J=1 Hz), 10.03 (1H, d, J=1 Hz).

MS (m/e): 148 (M⁺+1)

REFERENCE EXAMPLE 4

Production of 2,4-dichloro-thiazol-4-yl-carboaldehyde of the formula

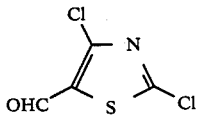

To a solution of dimethylformamide (73.1 g) in dichloroethylene (200 ml) was added dropwise phosphorus oxychloride (122.7 g) under ice-cooling, followed by stirring for 30 minutes (for preparation of Vilsmeier reagent). The resultant solution was admixed with thiazolin-2,4-dione (23.4 g) and heated for 1 hour under refluxing. The reaction solution obtained was cooled to ambient temperature, poured onto ice (200 g), neutralized by addition of sodium acetate and then extracted 3 times with 200 ml-portions of methylene chloride. The resultant extract in methylene chloride was washed with a small volume of saturated aqueous sodium hydrogen carbonate, dried over anhydrous magnesium sulfate, and then concentrated under reduced pressure. The residue obtained was purified chromatographically on a column of silica-gel as developed with benzene-ethyl acetate (10:1) as eluent. 4-Chloro-thiazol-5-yl-carboaldehyde (0.34 g) was afforded, and the titled compound (2.05 g) was also obtained as light yellow colored crystals.

NMR, δ (CDCl₃): 9.90 (1H, s)

MS (m/e): 182 (M⁺+1)

REFERENCE EXAMPLE 5

Production of 7-phenylacetamido-3-[2-(4-chlorothiazol-5-yl)vinyl]-3-cephem-4-carboxylic acid (cis-isomer) p-methoxybenzyl ester p-Methoxybenzyl 7-phenylacetamido-3-chloromethyl-3-cephem-4-carboxylate (3.265 g, 6.71 mmol) and triphenylphosphine (1.859 g, 7.05 mmol) were dissolved in dimethylformamide (20 ml). The resultant solution was admixed with sodium iodide (1.056 g, 7.05 mmol) at ambient temperature and stirred for 2 hours. The reaction solution obtained was concentrated to dryness under reduced pressure, and the residue was taken up into methylene chloride (10 ml). To the resultant solution in methylene chloride were added 4-chloro-thiazol-5-yl-carboaldehyde (1.100 g) which was obtained in Reference Example 3 described hereinbefore, and then saturated aqueous sodium hydrogen carbonate (10 ml). The mixture obtained was stirred for 6 hours at ambient temperature and then was left until it separated into the aqueous phase and organic phase. The aqueous phase as separated was extracted with methylene chloride (10 ml). The extract in methylene chloride and the organic solvent phase were combined together, dried over anhydrous magnesium sulfate and concentrated under reduced pressure. The residue obtained was purified by flash-column chromatography on a column of silica-gel (Wako-gel C-300) as developed with benzene-ethyl acetate (5:1) as eluent solvent. The titled compound was obtained (yield 2.891 g, 74%).

NMR, δ (CDCl₃): 3.15 (1H, d, J=18 Hz), 3.42 (1H, d=18 Hz), 3.61 (2H, s), 3.74 (3H, s), 5.00 (1H, d, J=5 Hz), 5.06 (2H, s), 5.84 (1H, dd, J=5 Hz, 9 Hz), 6.14 (1H, d, J=9 Hz), 6.27 (1H, d, J=12 Hz), 6.56 (1H, d, J=12 Hz), 6.7–6.75 (2H, m), 7.05–7.4 (7H, m), 8.50 (1H, s).

REFERENCE EXAMPLE 6

Production of 7-amino-3-[2-(4-chlorothiazol-5-yl) vinyl]-3-cephem-4-carboxylic acid (cis-isomer) p-methyoxybenzyl ester p-Methoxybenzyl 7-phenylacetamido-3-[2-(4-chlorothiazol-5-yl)vinyl]-3-cephem-4-carboxylate (cis-isomer) (2.452 g, 4.21 mmol) as prepared in the above Reference Example 5 was dissolved in methylene chloride (10 ml). The resultant solution was poured into a solution of phosphorus pentachloride (2.630 g, 12.63 mmol) and pyridine (3.4 ml, 42 mmol) in methylene chloride (40 ml) at −30° C. under cooling. The reaction solution obtained was stirred for 3 hours under ice-cooling and poured into methanol (40 ml) as pre-cooled to −30° C., followed by stirring the resultant mixture for 1 hour at ambient temperature. The mixture was then added into a mixture of saturated aqueous sodium chloride (100 ml) and methylene chloride (100 ml) and stirred for 1 hour. The mixture obtained was left until it separated into the aqueous phase and organic solvent phase. The aqueous phase was separated and extracted with methylene chloride (50 ml). The extract in methylene chloride was added to the above organic solvent phase, which was then washed with saturated aqueous sodium hydrogen carbonate, dried over anhydrous magnesium sulfate and concentrated under reduced pressure. The residue obtained was purified by flash-column chromatography on a column of silica-gel (Wako-gel C-300) as developed with benzene-ethyl acetate (3:1) as eluent. The titled compound was obtained (yield 1.543 g, 79%).

NMR, δ (CDCl$_3$): 1.75 (2H, broad s), 3.20 (1H, d, J=18 Hz), 3.44 (1H, d, J=18 Hz), 3.75 (3H, s), 4.77 (1H, d, J=5 Hz), 4.97 (1H, d, J=5 Hz), 5.08 (2H, s), 6.31 (1H, d, J=12 Hz), 6.53 (1H, d, J=12 Hz), 6.7–6.85 (2H, m), 7.1–7.25 (2H, m), 8.50 (1H, s).

REFERENCE EXAMPLE 7

Production of 7-phenylacetamido-3-[2-(2,4-dichlorothiazol-5-yl)vinyl]-3-cephem-4-carboxylic acid (cis-isomer) p-methoxybenzyl ester p-Methoxybenzyl 7-phenylacetamido-3-chloromethyl-3-cephem-4-carboxylate was reacted with 2,4-dichloro-thiazol-5-yl-carboaldehyde as obtained in the Reference Example 4, in the same manner as in the Reference Example 5. The titled compound was produced in a yield of 78%.

NMR, δ (CDCl$_3$): 3.19 (1H, d, J=18 Hz), 3.40 (1H, d, J=18 Hz), 5.01 (1H, d, J=5 Hz), 5.09 (2H, s), 5.88 (1H, dd, J=5 Hz, 9 Hz), 6.10 (1H, d, J=9Hz), 6.22 (1H, d, J=12 Hz), 6.46 (1H, d, J=12 Hz), 7.7–7.85 (2H, m), 7.1–7.45 (7H, m).

REFERENCE EXAMPLE 8

Production of 7-amino-3-[2-(2,4-dichlorothiazol-5-yl vinyl]-3-cephem-4-carboxylic acid (cis-isomer) p-methoxybenzyl ester p-Methoxybenzyl 7-phenylacetamido-3-[2-(2,4-dichlorothiazol-5-yl)vinyl]-3-cephem-4-carboxylate (cis-isomer) was treated with phosphorus pentachloride and pyridine in the same manner as in the Reference Example 6 to afford the titled compound in a yield of 73%.

NMR, δ (CDCl$_3$): 1.80 (2H, broad s), 3.20 (1H, d, J=18 Hz), 3.42 (1H, d, J=18 Hz), 3.75 (3H, s), 4.79 (1H, d, J=5 Hz), 4.98 (1H, d, J=5 Hz), 5.10 (2H, s), 6.26 (1H, d, J=12 Hz), 6.44 (1H, d, J=12 Hz), 7.7–7.85 (2H, m), 7.1–7.4 (7H, m).

EXAMPLE 20

Production of 7-[2-methoxyimino-2-(2-tritylaminothiazol-4-yl)acetamido]-3-[2-(4-chlorothiazol-5-yl)vinyl]-3-cephem-4-carboxylic acid (syn-isomer, cis-isomer) p-methoxybenzyl ester p-Methoxybenzyl 7-amino-3-[2-(4-chlorothiazol-5-yl)vinyl]-3-cephem-4-carboxylate (cis-isomer) (1.205 g, 2.60 mmol) and 2-(2-tritylaminothiazol)-2-methoxyimino-acetic acid (syn-isomer) (1.153 g, 2.60 mmol) were dissolved in methylene chloride (30 ml), to which were added pyridine (0.84 ml, 10.4 mmol) and then phosphorus oxychloride (0.33 ml, 3.64 mmol) at −20° C. under cooling. The reaction solution was stirred for 20 minutes at 0° C. and poured into a mixture of ice-water (100 ml) and ethyl acetate (100 ml), followed by stirring. The mixture obtained was allowed to stand until it separated into the aqueous phase and organic phase. The organic phase was separated from the aqueous phase, washed with saturated aqueous sodium hydrogen carbonate, dried over anhydrous magnesium sulfate and then concentrated under reduced pressure. The residue obtained was purified by flash-column chromatography on a column of silica-gel (Wako-gel C-300) (50 g) as developed with benzene-ethyl acetate (5:1) as eluent. The titled compound was obtained (yield 1.665 g, 72%).

NMR, δ (CDCl$_3$): 3.20 (1H, d, J=18 Hz), 3.44 (1H, d, J=18 Hz), 3.76 (3H, s), 4.03 (3H, s), 5.07 (2H, s), 5.08 (1H, d, J=5 Hz), 5.94 (1H, dd, J=5 Hz, 9 Hz), 6.33 (1H, d, J=12 Hz), 6.59 (1H, d, J=12 Hz), 6.7–7.4 (22H, m), 8.50 (1H, s).

EXAMPLE 21

Production of 7-[2-methoxyimino-2-(2-aminothiazol-4-yl)acetamido]-3-[2-(4-chlorothiazol-5-yl)vinyl]-3-cephem-4-carboxylic acid (syn-isomer, cis-isomer) sodium salt p-Methoxybenzyl 7-[2-methoxyimino-2-(2-tritylaminothiazol-4-yl)acetamido-3-[2-(4-chlorothiazol-5-yl)vinyl]-3-cephem-4-carboxylate syn-isomer, cis-isomer) (0.856 g, 0.962 mmol) was dissolved in anisole (2 ml), to which was added dropwise trifluoroacetic acid (8 ml) under ice-cooling. The mixture obtained was stirred for 1 hour under ice-cooling and then admixed with isopropyl ether (50 ml) to deposit a precipitate. The precipitate was removed by filtration, washed with isopropyl ether and dried under reduced pressure. The titled compound (the carboxylic acid) was obtained in the form of its trifluoroacetate (0.586 g) (as an acid-addition salt with trifluoroacetic acid). The compund obtained was mixed water (3 ml) and sodium hydrogen carbonate (0.242 g), and the resulting solution was purified by column-chromatography on a column of Diaion HP-20 as eluted with water and then with 30% aqueous acetone. The fractions of the eluate containing the desired compound were combined together and concentrated under reduced pressure, followed by lyophilization. The titled compound was obtained (yield 0.433 g, 82%).

NMR, δ (D$_2$O): 3.43 (1H, d, J=18 Hz), 3.70 (1H, d, J=18 Hz), 4.03 (3H, s), 5.42 (1H, d, J=5 Hz), 5.90 (1H, d, J=5 Hz), 6.48 (1H, d, J=12 Hz), 6.71 (1H, d, J=12 Hz), 7.06 (1H, s), 8.87 (1H, s).

EXAMPLE 22

Production of 7-[2-methoxyimino-2-(2-aminothiazol-4-yl)acetamido]-3-[2-(4-chlorothiazol-5-yl)vinyl]-3-cephem-4-carboxylic acid (syn-isomer, cis-isomer) pivaloyloxymethyl ester 7-[2-Methoxyimino-2-aminothiazol-4-yl)acetamido]-3-[2-(4-chlorothiazol-5yl-)vinyl]-3-cephem-4-carboxylic acid (syn-isomer, cis-isomer) sodium salt (0.104 g, 0.188 mmol) was dissolved in dimethylformamide (3 ml). Under ice-cooling, the resultant solution was admixed with a solution of iodomethyl pivalate in dimethylformamide (1 ml), and the mixture obtained was stirred for 10 minutes. To the reaction solution were added ice-water (20 ml) and ethyl acetate (20 ml). The resulting mixture was well agitated and then allowed to stand until it separated into the aqueous phase and organic phase. The organic phase was separated from the aqueous phase, washed twice with 10 ml-portions of water and with 10 ml of saturated aqueous sodium chloride, dried over anhydrous magnesium sulfate and then concentrated under reduced pressure. The residue obtained was purified by flash-column chromatography on a column of silica-gel (Wako-gel C-300) (10 g) as eluted with ethyl acetate. The titled compound was afforded (yield 0.940 g, 78%).

NMR, δ (CDCl₃): 1.13 (9H, s), 3.30 (1H, d, J=18 Hz), 3.51 (1H, d, J=18 Hz), 5.17 (1H, d, J=5 Hz), 5.43 (2H, broad s), 5.75 (1H, d, J=6 Hz), 5.80 (1H, d, J=6 Hz), 6.06 (1H, dd, J=5 Hz), 6.40 (1H, d, J=12 Hz), 6.66 (1H, d, J=12 Hz), 6.78 (1H, s), 7.65 (1H, d, J=9 Hz), 8.54 (1H, s).

EXAMPLE 23-28

The following compounds were produced in the same manner as in Example 20 described above.

Example 23

7-[2-methoxyimino-2-(2-tritylaminothiazol-4-yl)acetamido]-3-[2-(thiazol-2-yl)vinyl]-3-cephem-4-carboxylic acid (syn-isomer, trans-isomer) diphenylmethyl ester (Yield 72%).

NMR, δ (CDCl₃): 3.45 (1H, d, J=18 Hz), 3.67 (1H, d, J=18 Hz), 4.04 (3H, s), 5.16 (1H, d, J=5 Hz), 5.97 (1H, dd, J=5 Hz, 9 Hz), 6.58 (1H, s), 6.73 (1H, s), 6.85 (1H, s), 6.9–7.5 (29H, m), 7.74 (1H, d, J=3 Hz).

EXAMPLE 24

7-[2-methoxyimino-2-(2-tritylaminothiazol-4-yl)acetamino]-3-[2-(2-methylthiazol-5-yl)vinyl]-3-cephem-4-carboxylic acid (syn-isomer, trans-isomer) diphenylmethyl ester (Yield 68%).

NMR, δ (CDCl₃): 2.63 (3H, s), 3.56 (2H, broad s), 4.04 (3H, s), 5.06 (1H, d, J=5 Hz), 5.88 (1H, dd, J=5 Hz, 9 Hz), 6.73 (1H, s), 6.82 (1H, d, J=16 Hz), 6.98 (1H, s), 7.0–7.5 (H29, m). EXAMPLE 25

7-[2-methoxyimino-2-(2-tritylaminothiazol-4-yl)acetamido]-3-[2-(2-methylthiazol-5-yl)vinyl]-3-cephem-4-carboxilyc acid (syn-isomer, cis-isomer) diphenylmethyl ester (Yield 76%).

NMR, δ (CDCl₃): 2.60 (3H, s), 3.27 (1H, d, J=18 Hz), 3.48 (1H, D, J=18 Hz), 4.04 (3H, s), 5.16 (1H, d, J=5 Hz), 5.97 (1H, dd, J=5 Hz, 9 Hz), 6.13 (1H, d, J=12 Hz), 6.41 (1H, d, J=12 Hz), 6.71 (1H, s), 6.85 (1H, s), 6.9–7.5 (28H, m).

EXAMPLE 26

7-[2-methoxyimino-2-(2-tritylaminothiazol-4-yl)acetamidol]-3-[2-(thiazol-4-yl)vinyl]-3-cephem-4-carboxylic acid (syn-isomer, cis-isomer) p-methoxybenzyl ester (Yield 75%).

NMR, δ (CDCl₃): 3.40 (1H, d, J=18 Hz), 3.62 (1H, d, J=18 Hz), 3.77 (3H, s), 4.04 (3H, s), 5.10 (1H, d, J=5 Hz), 5.11 (2H, s), 5.89 (1H, dd, J=5 Hz), 9 Hz), 6.53 (2H, s), 6.7–7.5 (23H, m), 8.66 (1H, d, J=2Hz).

EXAMPLE 27

7-[2-methoxyimino-2-(2-tritylaminothiazol-4-yl)acetamido]-3-[2-(thiazol-5-yl)vinyl]-3-cephem-4-carboxylic acid (syn-isomer, cis-isomer) diphenylmethyl ester (Yield 69%).

NMR, δ (CDCl₃): 3.27 (1H, d, J=18 Hz), 3.46 (1H, d, J=18 Hz), 4.04 (1H, d, J=5 Hz), 5.96 (1H, dd, J=5 Hz, 9 Hz), 6.23 (1H, d, J=12 Hz), 6.50 (1H, d, J=12 Hz), 6.71 (1H, s), 6.83 (1H, s), 6.9–7.5 (27H, m), 7.61 (1H, s), 8.57 (1H, s).

EXAMPLE 28

7-[2-methoxyimino-2-(2-tritylaminothiazol-4-yl)acetamido]-3-[2-(2,4-dichlorothiazol-5-yl)vinyl]-3-cephem-4-carboxylic acid (syn-isomer, cis-isomer) p-methoxybenzyl ester (Yield 81%).

NMR, δ (CDCl₃): 3.21 (1H, d, J=18Hz), 3.42 (1H, d, J=18 Hz), 3.76 (3H, s), 4.04 (3H, s), 5.09 (1H, d, J=5 Hz), 5.11 (2H, s), 5.95 (1H, dd, J=5 Hz, 9 Hz), 6.25 (1H, d, J=12 Hz), 6.47 (1H, d, J=12 Hz), 6.7–7.4 (22H, m).

EXAMPLE 29-34

The following compounds in the form of sodium salt or trifluoroacetate were produced in the same manner as in the foregoing Example 21.

EXAMPLE 29

7-[2-methoxyimino-2-(2-aminothiazol-4-yl)acetamido]-3-[2-(thiazol-2-yl)vinyl]-3-cephem-4-carboxylic acid (syn-isomer, trans-isomer) sodium salt (Yield 82%).

NMR, δ (D₂O): 3.82 (2H, broad s), 4.02 (3H, s), 5.32 (1H, d, J=5 Hz), 5.85 (1H, d, J=5 Hz), 6.99 (1H, d, J=16 Hz), 7.03 (1H, s), 7.46 (1H, d, J=16 Hz), 7.49 (1H, d, J=3 Hz), 7.76 (1H, d, J=3 Hz).

EXAMPLE 30

7-[2-methoxyimino-2-(2-aminothiazol-4-yl)acetamido]-3-[2-(2-methylthiazo-5-yl)vinyl]-3-cephem-4-carboxylic acid (syn-isomer, trans-isomer) trifluoroacetate (Yield 88%).

NMR, δ (CD₃SOCD₃): 2.62 (3H, s), 3.75 (2H, broad s), 3.83 (3H, s), 5.18 (1H, d, J=5 Hz), 5.75 (1H, dd, J=5 Hz, 9 Hz), 6.75 (1H, s), 7.13 (2H, s), 7.60 (1H, s), 9.58 (1H, d, J=9 Hz).

EXAMPLE 31

7-[2-methoxyimino-2-(2-aminothiazol-4-yl)acetamido]-3-[2-(2-methylthiazol-5-yl)vinyl]-3-cephem-4-carboxylic acid (syn-isomer, cis-isomer) trifluoroacetate (Yield 78%).

NMR, δ (CD₃SOCD₃): 2.59 (3H, s), 3.41 (1H, d, J=18 Hz), 3.53 (1H, d, J=18 Hz), 3.84 (3H, s), 5.28 (1H, d, J=5 Hz), 5.82 (1H, dd, J=5 Hz, J=9 Hz), 6.22 (1H, d, J=12 Hz), 6.63 (1H, d, J=12 Hz), 6.73 (1H, s), 7.57 (1H, s), 9.60 (1H, d, J=9 Hz).

EXAMPLE 32

7-[2-methoxyimino-2-(2-aminothiazol-4-yl)acetamido]-3-[2-(thiazol-4-yl)vinyl]-3-cephem-4-carboxylic acid (syn-isomer, cis-isomer) sodium salt (Yield 74%).

NMR, δ (D₂O): 3.45 (1H, d, J=18 Hz), 3.58 (1H, d, J=18 Hz), 4.03 (3H, s), 5.33 (1H, d, J=5 Hz), 5.84 (1H, d, J=5 Hz), 6.56 (1H, d, J=12 Hz), 6.71 (1H, d, J=12 Hz), 7.06 (1H, s), 7.51 (1H, d, J=2 Hz), 8.99 (1H, d, J=2 Hz).

EXAMPLE 33

7-[2-methoxyimino-2-(2-aminothiazol-4-yl)acetamido]-3-[2-(thiazol-5-yl)vinyl]-3-cephem-4-carboxylic acid (syn-isomer, cis-isomer) sodium salt (Yield 78%).

NMR, δ (D₂O): 3.48 (1H, d, J=18 Hz), 3.70 (1H, d, J=18 Hz), 4.05 (1H, s), 5.45 (1H, d, 2J=5 Hz), 5.90 (1H, d, J=5 Hz), 6.39 (1H, d, J=12 Hz), 6.81 (1H, d, J=12 Hz), 7.08 (1H, s), 7.86 (1H, s), 8.90 (1H, s).

EXAMPLE 34

7-[2-methoxyimino-2-(2-aminothiazol-4-yl)acetamido]-3-[2-(2,4-dichlorothiazol-5-yl)vinyl]-3-cephem-4-carboxylic acid (syn-isomer, cis-isomer) sodium salt (Yield 78%).

NMR, δ (D₂O): 3.46 (1H, d, J=18 Hz), 3.67 (1H, d, J=18 Hz), 4.04 (3H, s), 5.43 (1H, d, J=5 Hz), 5.91 (1H, d, J=5 Hz), 6.45 (1H, d, J=12 Hz), 6.64 (1H, d, J=12 Hz), 7.08 (1H, s).

EXAMPLES 35–39

The following compounds were produced in the same manner as in Example 22 described hereinbefore.

EXAMPLE 35

7-[2-methoxyimino-2-(2-aminothiazol-4-yl)acetamido]-3-[2-(2-methylthiazol-5-yl)vinyl]-3-cephem-4-carboxylic acid (syn-isomer, trans-isomer) (5-methyl-2-oxo-1,3-dioxolen-4-yl)methyl ester (Yield 62%).

NMR, δ (CDCl$_3$): 2.21 (3H, s), 2.69 (3H, s), 3.65 (1H, d, J=18 Hz), 3.75 (1H, d, J=18 Hz), 4.04 (3H, s), 4.93 (1H, d, J=16 Hz), 5.12 (1H, J=5 Hz), 5.14 (1H, d, J=16 Hz), 5.14 (2H, broad), 5.99 (1H, dd, J=5 Hz, J=9 Hz), 6.81 (1H, s), 6.92 (1H, d, J=16 Hz), 7.24 (1H, d, J=16 Hz), 7.53 (1H, s), 7.64 (1H, d, J=9 Hz).

EXAMPLE 36

7-[2-methoxyimino-2-(2-aminothiazol-4-yl)acetamido]-3-[2-(2-methylthiazol-5-yl)vinyl]-3-cephem-4-carboxylic acid (syn-isomer, cis-isomer) (5-methyl-2-oxo-1,3-dioxolen-4-yl)methyl ester (Yield 69%).

NMR, δ (CDCl$_3$): 2.08 (3H, s), 2.64 (3H, s), 3.45 (1H, d, J=18 Hz), 3.54 (1H, d, J=18 Hz), 4.04 (3H, s), 4.80 (1H, d, J=16 Hz), 4.99 (1H, d, J=16 Hz), 5.22 (1H, d, J=5 Hz), 5.4 (2H, broad), 6.10 (dd, J=5 Hz, 9 Hz), 6.17 (1H, d, J=12 Hz), 6.60 (1H, d, J=12 Hz), 6.78 (1H, s), 7.46 (1H, s), 7.72 (1H, d, J=9 Hz).

EXAMPLE 37

7-[2-methoxyimino-2-(2-aminothiazol-4-yl)acetamido]-3-[2-(thiazol-4-yl)vinyl]-3-cephem-4-carboxylic acid (syn-isomer, cis-isomer) pivaloyloxymethyl ester (Yield 72%).

NMR, δ (CDCl$_3$): 1.16 (9H, s), 3.48 (1H, d, J=18 Hz), 3.68 (1H, d, J=18 Hz), 4.04 (3H, s), 5.16 (1H, d, J=5 Hz), 5.75 (1H, d, J=6 Hz), 5.86 (1H, d, J=6 Hz), 5.94 (1H, dd, J=5 Hz, 9 Hz), 6.51 (1H, d, J=12 Hz), 6.58 (1H, d, J=12 Hz), 6.88 (1H, s), 7.19 (1H, d, J=2 Hz), 8.66 (1H, d, J=2 Hz).

EXAMPLE 38

7-[2-methoxyimino-2-(2-aminothiazol-4-yl)acetamido]-3-[2-(thiazol-5-yl)vinyl]-3-cephem-4-carboxylic acid (syn-isomer, cis-isomer) pivaloyloxymethyl ester (Yield 76%).

NMR, δ (CDCl$_3$): 1.13 (9H, s), 3.32 (1H, d, J=18 Hz), 3.50 (1H, d, J=18 Hz), 4.04 (3H, s), 5.19 (1H, d, J=5 Hz), 5.74 (1H, d, J=6 Hz), 5.81 (1H, d, J=6 Hz), 6.02 (1H, dd, J=5 Hz, 9 Hz), 6.35 (1H, d, J=12 Hz), 6.68 (1H, d, J=12 Hz), 6.88 (1H, s), 7.41 (1H, d, J=9 Hz), 7.75 (1H, s), 8.66 (1H, s).

EXAMPLE 39

7-[2-methoxyimino-2-(2-aminothiazol-4-yl)acetamido]-3-[2-(2,4-dichlorothiazol-5-yl)vinyl]-3-cephem-4-carboxylic acid (syn-isomer, cis-isomer) pivaloyloxymethyl ester (Yield 71%).

NMR, δ (CDCl$_3$): 1.16 (9H, s), 3.30 (1H, d, J=18 Hz), 3.52 (1H, d, J=18 Hz), 4.05 (3H, s), 5.16 (1H, d, J=6 Hz), 5.78 (1H, d, J=6 Hz), 5.81 (1H, d, J=6 Hz), 6.05 (1H, dd, J=5 Hz, 9 Hz), 6.38 (1H, d, J=12 Hz), 6.58 (1H, d, J=12 Hz), 6.91 (1H, s).

What we claim is:

1. A cephalosporin compound of the formula (I)

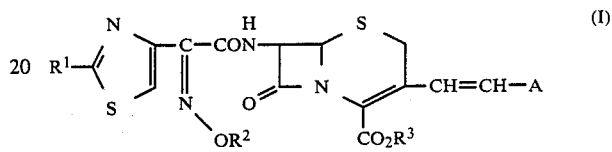

wherein $R^1$ is an amino group or a protected amino group; $R^2$ is a lower alkyl group, a carboxymethyl group or a protected carboxymethyl group; $R^3$ is a hydrogen atom, a salt-forming cation or a carboxyl-protecting group; A is thiazolyl group, a lower-alkyl-thiazolyl group, a halo-thiazolyl group, or a 3-lower-alkylthiazolio group optionally substituted with one lower alkyl group, with an iodide or tirfluoroacetate counterion, and a pharmaceutically acceptable salt or ester of said cephalosporin compound.

2. A cephalosporin compound as claimed in claim 1 which if of the formula (Ic)

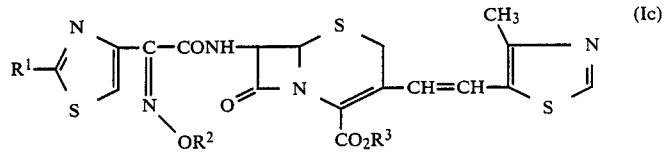

wherein $R^1$ is an amino group or a protected amino group, $R^2$ is a lower alkyl group, a carboxymethyl group or a protected carboxymethyl group, and $R^3$ is a hydrogen atom, a salt-forming cation or a carboxyl-protecting group.

3. A cephalosporin compound as claimed in claim 1 which is of the formula (Id)

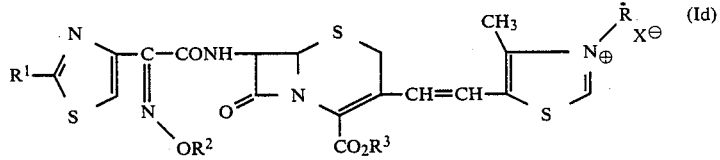

wherein $R^1$ is an amino group or a protected amino group, $R^2$ is a lower ($C_1$–$C_6$) alkyl group, a carboxymethyl group or a protected carboxymethyl group, $R^3$ is a hydrogen atom, a salt-forming cation or a carboxyl-protecting group, R is a lower alkyl group and X is an iodide ion or a trifluoroacetate ion.

4. A cephalosporin compound as claimed in claim 1 which is of the formula (Ie)

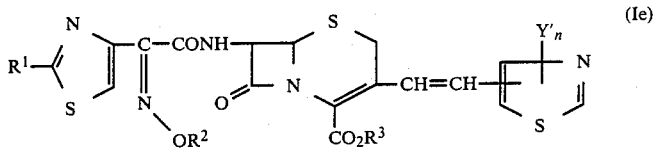

(Ie)

wherein $R^1$ is an amino group or a protected amino group, $R^2$ is a lower ($C_1$–$C_3$) alkyl group, a carboxymethyl group, or a protected carboxymethyl group, $R^3$ is a hydrogen atom, a salt-forming cation or a carboxyl-protecting group, and Y' is a hydrogen atom or a halogen atom, and n is a whole number of 1 or 2.

5. A cephalosporin compound as claimed in claim 1 which is of the formula (If)

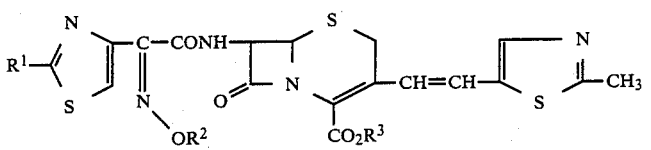

(If)

wherein $R^1$ is an amino group or a protected amino group, $R^2$ is a lower ($C_1$–$C_6$) alkyl group, a caroboxymethyl group or a protected carboxymethyl group, and $R^3$ is a hydrogen atom, a salt-forming cation or a carboxyl-protecting group.

6. A compound as claimed in claims 1, 2, 3, 4 or 5 in which $R^1$ is an amino group, $R^2$ is a methyl group or a carboxymethyl group, and $R^3$ is sodium atom, benzhydryl group, p-methoxybenzyl group, diphenylmethyl group, pivaloyloxymethyl group or (5-methyl-2-oxo-1,3-dioxolene-4-yl)-methyl group.

7. A compound as claimed in claim 1 which is selected from the group consisting of
7-[2-methoxyimino-2-(2-aminothiazol-4-yl)acetamido]-3-[2-(thiazol-2-yl)vinyl]-3-cephem-4-carboxylic acid (syn-isomer, trans-isomer, or syn-isomer, cis-isomer);
7-[2-methoxyimino-2-(2-aminothiazol-4-yl)acetamido]-3-[2-(thiazol-4-yl)vinyl]-3-cephem-4-carboxylic acid (syn-isomer, cis-isomer) and its sodium salt and its pivaloyloxymethyl ester; and
7-[2-methoxyimino-2-(2-aminothiazol-4-yl)acetamido]-3-[2-(thiazol-5-yl)vinyl]-3-cephem-4-carboxylic acid (syn-isomer, cis-isomer), it sodium salt, and its pivaloyloxymethyl ester.

8. A compound as claimed in claim 1 which is selected from the group of consisting of
7-[2-carboxymethoxyimino-2-(2-aminothiazol-4-yl)acetamido]-3-[2-(4-methylthiazol-5-yl)vinyl]-3-cephem-4-carboxylic acid (syn-isomer, trans-isomer, or syn-isomer, cis-isomer) and its acid addition salt with trifluoroacetic acid,
7-[2-t-butoxycarbonylmethoxyimino-2-(2-tritylaminothiazol-4-yl)acetamido]-3-[2-(4-methylthiazol-5-yl)vinyl]-3-cephem-4-carboxylic acid (syn-isomer, trans-isomer, or syn-isomer, cis-isomer); and
7-[2-methoxyimino-2-(2-aminothiazol-4-yl)acetamido]-3-[2-(2-methylthiazol-5-yl)vinyl]-3-cephem-4-carboxylic acid (syn-isomer, trans-isomer, or syn-isomer, cis-isomer), its sodium salt, its acid addition salt with trifluoroacetic acid, and its (5-methyl-2-oxo-1,3-dioxolene-4-yl)-methyl ester.

9. A compound as claimed in claim 1 which is selected from the group consisting of
7-[2-methoxyimino-2-(2-aminothiazol-4-yl)acetamido]-3-[2-(4-chlorothiazol-5-yl)vinyl]-3-cephem-4-carboxylic acid (syn-isomer, cis-isomer), its sodium salt and its pivaloyloxymethyl ester; and
7-[2-methoxyimino-2-(2-aminothiazol-4-yl)acetamido]-3-[2-(2,4-dichlorothiazol-5-yl)vinyl]-3-cephem-4-carboxylic acid (syn-isomer, cis-isomer), it sodium salt and its pivaloyloxymethyl ester.

10. A compound as claimed in claim 1 which is 7-[2-methoxyimino-2-(2-aminothiazol-4-yl)acetamido]-3-[2-(3,4-dimethyl-5-thiazolio)vinyl]-3-cephem-4-carboxylic acid (syn-isomer, trans-isomer, or syn-isomer, cis-isomer) iodide or its acid addition salt with trifluoroacetic acid.

11. 7-[2-methoxyimino-2-(2-aminothiazol-4-yl)acetamido]-3-[2-(4-methylthiazol-5-yl)vinyl]-3-cephem-4-carboxylic acid (syn-isomer, cis-isomer) sodium salt.

12. 7-[2-methoxyimino-2-(2-aminothiazol-4-yl)acetamido]-3-[2-(4-methylthiazol-5-yl)vinyl]-3-cephem-4-carboxylic acid (syn-isomer, cis-isomer) pivaloyloxymethyl ester.

13. A compound which is selected from the group consisting of 7-[2-methoxyimino-2-(2-aminothiazol-4-yl)acetamido-3-[2-(4-methylthiazol-5-yl)vinyl]-3-cephem-4-carboxylic acid (syn-isomer, trans-isomer, or syn-isomer, cis-isomer), a sodium salt thereof, a pivaloyloxymethyl ester thereof, a (5-methyl-2-oxo-1,3-dioxolene-4-yl)-methyl ester thereof and an acid addition salt thereof with trifluoroacetic acid.

14. A pharmaceutical, antibacterial composition which comprises an antibacterially effective amount of the compound of the formula (I) as defined in claim 1 or the compound of the formula (Ic) to (If) as defined in anyone of claims 2 to 5 or a pharmaceutically acceptable salt or ester thereof, as the active ingredient, in combination with a pharmaceutically acceptable carrier for the active ingredient.

* * * * *

UNITED STATES PATENT AND TRADEMARK OFFICE

(12)            CERTIFICATE EXTENDING PATENT TERM
UNDER 35 U.S.C. § 156

| | | |
|---|---|---|
| (68) PATENT NO. | : | 4,839,350 |
| (45) ISSUED | : | June 13, 1989 |
| (75) INVENTOR | : | Kunio Atsumi, et al. |
| (73) PATENT OWNER | : | Meiji Seika Kaisha, Ltd. |
| (95) PRODUCT | : | SPECTRACEF® |

This is to certify that an application under 35 U.S.C. § 156 has been filed in the United States Patent and Trademark Office, requesting extension of the term of U.S. Patent No. 4,839,350 based upon the regulatory review of the product SPECTRACEF® by the Food and Drug Administration. Since it appears that the requirements of the law have been met, this certificate extends the term of the patent for the period of

(94)            1,036 days from June 13, 2006, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 25th day of January 2006.

Jon W. Dudas
Under Secretary of Commerce for Intellectual Property and Director of the United States Patent and Trademark Office